US010596229B2

(12) United States Patent
Johansen

(10) Patent No.: US 10,596,229 B2
(45) Date of Patent: *Mar. 24, 2020

(54) METHOD OF TREATING DIABETES MELLITUS BY ADMINISTRATION, AT SPECIFICALLY DEFINED INTERVALS, OF A DERIVATIVE OF A NATURALLY OCCURRING INSULIN OR INSULIN ANALOGUE, THE DERIVATIVE HAVING A PROLONGED PROFILE OF ACTION

(71) Applicant: Novo Nordisk A/S, Bagsvaerd (DK)

(72) Inventor: Thue Johansen, Koebenhavn OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,680

(22) Filed: Nov. 13, 2017

(65) Prior Publication Data

US 2018/0125946 A1    May 10, 2018

Related U.S. Application Data

(63) Continuation of application No. 13/881,173, filed as application No. PCT/EP2011/068870 on Oct. 27, 2011, now abandoned.

(60) Provisional application No. 61/407,206, filed on Oct. 27, 2010, provisional application No. 61/498,645, filed on Jun. 20, 2011.

(30) Foreign Application Priority Data

Oct. 27, 2010  (EP) .................................... 10189115
Oct. 27, 2010  (EP) .................................... 11170366

(51) Int. Cl.
*A61K 38/28* (2006.01)
*C07K 14/62* (2006.01)

(52) U.S. Cl.
CPC .............. *A61K 38/28* (2013.01); *C07K 14/62* (2013.01)

(58) Field of Classification Search
CPC ..................................................... C07K 14/62
See application file for complete search history.

(56) References Cited

U.S. PATENT DOCUMENTS

| | | |
|---|---|---|
| 3,528,960 A | 9/1970 | Haas |
| 3,868,358 A | 2/1975 | Jackson |
| 3,907,676 A | 9/1975 | Jorgensen |
| 4,476,118 A | 10/1984 | Brange et al. |
| 4,669,430 A | 6/1987 | Reinold et al. |
| 4,876,322 A | 10/1989 | Budde et al. |
| 4,983,658 A | 1/1991 | Kress et al. |
| 5,177,058 A | 1/1993 | Dorschug |
| 5,382,574 A | 1/1995 | Jorgensen |
| 5,605,884 A | 2/1997 | Lee et al. |
| 5,646,242 A | 7/1997 | Baker et al. |
| 5,750,497 A | 5/1998 | Havelund et al. |
| 5,830,999 A | 11/1998 | Dunn |
| 5,866,538 A | 2/1999 | Norup et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,211,144 B1 | 4/2001 | Havelund |
| 6,221,837 B1 | 4/2001 | Ertl et al. |
| 6,251,856 B1 | 6/2001 | Markussen et al. |
| 6,335,316 B1 | 1/2002 | Hughes et al. |
| 6,451,762 B1 | 9/2002 | Havelund et al. |
| 6,451,970 B1 | 9/2002 | Schaffer et al. |
| 6,504,005 B1 | 1/2003 | Fridkin et al. |
| 6,620,780 B2 | 9/2003 | Markussen et al. |
| 6,652,886 B2 | 11/2003 | Ahn et al. |
| 6,869,930 B1 | 3/2005 | Havelund et al. |
| 7,229,964 B2 | 6/2007 | Markussen et al. |
| 7,402,565 B2 | 7/2008 | Kjeldsen et al. |
| 7,544,656 B2 | 6/2009 | Sabetsky |
| 7,615,532 B2 | 11/2009 | Jonassen et al. |
| 8,003,605 B2 | 8/2011 | Bayer et al. |
| 8,067,362 B2 | 11/2011 | Kodra et al. |
| 8,404,645 B2 | 3/2013 | Schlein |
| 8,691,759 B2 | 4/2014 | Madsen et al. |
| 8,722,620 B2 | 5/2014 | Fynbo et al. |
| 8,796,205 B2 | 8/2014 | Jonassen et al. |
| 8,828,923 B2 | 9/2014 | Jonassen et al. |
| 8,933,021 B2 | 1/2015 | Hubalek et al. |
| 8,962,794 B2 | 2/2015 | Madsen et al. |
| 9,034,818 B2 | 5/2015 | Poulsen et al. |
| 9,045,560 B2 | 6/2015 | Madsen et al. |

(Continued)

FOREIGN PATENT DOCUMENTS

| | | |
|---|---|---|
| AU | 2011252127 B2 | 2/2014 |
| CN | 1829738 A | 9/2006 |

(Continued)

OTHER PUBLICATIONS

Tambascia et al., "Degludec: the new ultra-long insulin analogue," Diabetology Metabol. Synd., 2015, vol. 7, pp. 1-7.

Hoevelmann U. et al., Insulin degludec 200 U/ml is ultra-lang-acting and has a flat and stable glucose-lowering effect, Diabetologia, 2012, vol. 55, No. Suppl. 1, pp. S374-S375, XP002723769 & 48th Annual Meeting of the European-Association-For-The-Study-Of-Diabetes; Berlin, Germany; Oct. 1-5, 2012.

Wang F. et al., Insulin degludec as an ultralong-acting basal insulin once a day: a systematic review, Diabetes, Metabolic Syndrome and Obesity: Targets and Therapy, 2012, vol. 5, pp. 191-204, XP002723770.

(Continued)

*Primary Examiner* — Gyan Chandra
(74) *Attorney, Agent, or Firm* — Rosemarie R. Wilk-Orescan

(57) ABSTRACT

The present invention relates to methods for treatment of a condition or disease where administration of insulin will be of benefit, comprising administering, to a patient in need thereof, effective dosages of an insulin, insulin analogue or derivative thereof, which exhibits a prolonged profile of action, wherein said dosages are administered at intervals of varying length.

9 Claims, 2 Drawing Sheets

(56) References Cited

U.S. PATENT DOCUMENTS

| | | | |
|---|---|---|---|
| 9,131,722 B2 | 9/2015 | Kim et al. |
| 9,447,163 B2 | 9/2016 | Mollerup et al. |
| 9,481,721 B2 | 11/2016 | Naver et al. |
| 9,603,904 B2 | 3/2017 | Johansen et al. |
| 9,688,737 B2 | 6/2017 | Madsen et al. |
| 9,839,579 B2 | 12/2017 | Weeks et al. |
| 9,884,094 B2 | 2/2018 | Johansen et al. |
| 10,137,172 B2 | 11/2018 | Johansen et al. |
| 2002/0045731 A1 | 4/2002 | Schaffer et al. |
| 2002/0155994 A1 | 10/2002 | Havelund et al. |
| 2003/0004096 A1 | 1/2003 | Boderke |
| 2003/0236196 A1 | 12/2003 | Kerwin et al. |
| 2004/0006000 A1 | 1/2004 | Langkjaer |
| 2004/0116345 A1 | 6/2004 | Besman et al. |
| 2004/0138099 A1 | 7/2004 | Draeger |
| 2005/0054818 A1 | 3/2005 | Brader et al. |
| 2005/0074866 A1 | 4/2005 | Grancha et al. |
| 2005/0222006 A1 | 10/2005 | Havelund et al. |
| 2005/0232899 A1 | 10/2005 | Balwani et al. |
| 2006/0183668 A1 | 8/2006 | Jonassen et al. |
| 2008/0076705 A1 | 3/2008 | Kodra et al. |
| 2009/0074882 A1 | 3/2009 | Havelund et al. |
| 2009/0137454 A1 | 5/2009 | Fynbo et al. |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |
| 2011/0230402 A1 | 9/2011 | Johansen et al. |
| 2011/0301081 A1 | 12/2011 | Becker et al. |
| 2014/0073759 A1 | 3/2014 | Mollerup et al. |
| 2014/0328943 A1 | 11/2014 | Havelund et al. |
| 2014/0349925 A1 | 11/2014 | Jonassen et al. |
| 2015/0126439 A1 | 5/2015 | Johansen et al. |
| 2015/0250857 A1 | 9/2015 | Andresen et al. |
| 2016/0058840 A1 | 3/2016 | Johansen et al. |
| 2016/0296602 A1 | 10/2016 | Johansen |
| 2017/0165327 A1 | 6/2017 | Andresen et al. |
| 2017/0319664 A1 | 11/2017 | Johansen |
| 2018/0125946 A1 | 5/2018 | Johansen |
| 2019/0160155 A1 | 5/2019 | Johansen |

FOREIGN PATENT DOCUMENTS

| | | |
|---|---|---|
| CN | 101389650 A | 12/2006 |
| CN | 101454019 A | 6/2009 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 925792 A2 | 6/1999 |
| EP | 1153608 A1 | 11/2001 |
| EP | 884053 B1 | 10/2002 |
| EP | 1283051 A1 | 2/2003 |
| EP | 0894095 | 5/2003 |
| EP | 0785713 B1 | 9/2003 |
| EP | 1595544 A1 | 11/2005 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | 38005689 | 5/1963 |
| JP | B S38-5689 | 5/1963 |
| JP | 1254699 | 5/1979 |
| JP | 57-067548 A | 4/1982 |
| JP | 02101022 | 4/1990 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521006 A | 11/2001 |
| JP | 2001-521904 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2004-523589 A | 8/2004 |
| JP | 2006-511441 A | 4/2006 |
| JP | 2006-519253 | 8/2006 |
| JP | 2007-523881 | 8/2007 |
| JP | 2009-522231 | 6/2009 |
| JP | 4808785 B2 | 11/2011 |
| JP | 4959005 B2 | 6/2012 |
| JP | 5026567 B2 | 9/2012 |
| JP | 5331071 B2 | 10/2013 |
| RU | 2160118 C2 | 12/2000 |
| RU | 2164520 C2 | 3/2001 |
| RU | 2352581 C2 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 97/31022 A1 | 8/1997 |
| WO | 98/02460 A1 | 1/1998 |
| WO | 98/05361 A2 | 2/1998 |
| WO | 98/42367 A1 | 10/1998 |
| WO | 98/42368 A1 | 10/1998 |
| WO | 98/47529 A1 | 10/1998 |
| WO | 99/21573 | 5/1999 |
| WO | 99/21578 | 5/1999 |
| WO | 99/21888 A1 | 5/1999 |
| WO | 99/22754 | 5/1999 |
| WO | 99/24071 A1 | 5/1999 |
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 2001/49314 A2 | 7/2001 |
| WO | 02076495 A1 | 10/2002 |
| WO | 2003/002136 A2 | 1/2003 |
| WO | 03/013573 | 2/2003 |
| WO | 03030829 A2 | 4/2003 |
| WO | 03/0053339 A2 | 7/2003 |
| WO | 03/053339 A2 | 7/2003 |
| WO | 03/094951 A1 | 11/2003 |
| WO | 03/094956 A1 | 11/2003 |
| WO | 2004/039392 A2 | 5/2004 |
| WO | 2004/112828 A1 | 12/2004 |
| WO | 2005/005477 A2 | 1/2005 |
| WO | 2005/012347 A2 | 2/2005 |
| WO | 2005/016365 A2 | 2/2005 |
| WO | 2005/021022 A2 | 3/2005 |
| WO | 2005/47508 A1 | 5/2005 |
| WO | 2005/063298 A1 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 06/51103 A2 | 5/2006 |
| WO | 2006/053906 A1 | 5/2006 |
| WO | 2006/079019 A2 | 7/2006 |
| WO | 2006/082204 | 8/2006 |

(56) References Cited

FOREIGN PATENT DOCUMENTS

| | | |
|---|---|---|
| WO | 2006/082205 | 8/2006 |
| WO | 2007/041481 A1 | 4/2007 |
| WO | 2007/074133 A2 | 7/2007 |
| WO | 2007096431 A1 | 8/2007 |
| WO | 2007/121256 A2 | 10/2007 |
| WO | 2007/128815 A1 | 11/2007 |
| WO | 2007/128817 A2 | 11/2007 |
| WO | 2007/135117 A2 | 11/2007 |
| WO | 2008/034881 A1 | 3/2008 |
| WO | 2008/152106 A1 | 12/2008 |
| WO | 2009/060071 A1 | 5/2009 |
| WO | 2009/063072 A2 | 5/2009 |
| WO | 2010/049488 A1 | 5/2010 |
| WO | 2011141407 A1 | 11/2011 |
| WO | 2012055967 A2 | 5/2012 |
| WO | 2012119007 A1 | 9/2012 |
| WO | 2013037754 A2 | 3/2013 |
| WO | 2013164375 A1 | 11/2013 |

OTHER PUBLICATIONS

Korsatko S. et al., Ultra-long-acting insulin degludec: bioequivalence and similar pharmacodynamics shown for two different formulations (U100 and U200), Diabetologia, 2011, vol. 54, No. Suppl. 1, XP002723771, p. S427, & 47th Annual Meeting of the European-Association-For-The-Study-Of-Diabetes (EASD); Lisbon, Portugal; Sep. 12-16, 2011.
American Diabetes Association,Standards of Medical Care in Diabetes 2012, Diabetes Care 2012,vol. 35(Suppl 1), pp. S11-S63.
American Diabetes Association. Insulin administration. Diabetes Care. 2012 vol. 35, No. 1, pp. S1-S2.
American Diabetes Association. Standards of Medical Care in Diabetes—2014. Diabetes Care. 2014, vol. 37 Suppl 1, pp. S14-S80.
Anderson RM et al. Patient empowerment: results of a randomized controlled trial. Diabetes Care. 1995, vol. 18,No. 7 pp. 943-949.
Barnett et al: Dosing of insulin glargine in the treatment of type 2 diabetes ,Clinical Therapeutics, 2007 vol. 29, No. 6,,pp. 987-999.
Benjamin EM. Self-monitoring of blood glucose: the basics. Clinical Diabetes. 2002, vol. 20, No. 1, pp. 45-47.
Canadian Diabetes Association Clinical Practice Guidelines Expert Committee. Canadian Diabetes Association. Canadian Journal of Diabetes. 2008, vol. 32(Suppl 1)pp. S1-S201.
Davies M, et al.. Improvement of glycemic control in subjects with poorly controlled type 2 diabetes. Diabetes Care. 2005,vol. 28, No. 6, pp. 1282-1288.
Deutsch T et al,Utopia: A Consultation System for Visit-By-Visit Diabetes Management, Medical Informatica. Taylor and Francis.; Basingstoke. GB, 1996, vol. 21, No. 4, pp. 345-358.
Duckworth W. et al.Glucose Control and Vascular Complications in Veterans with Type 2 Diabetes, The new england journal o f medicine, 2009, vol. 360, pp. 129-139.
Gerstein H C et al. A randomized trial of adding insulin glargine vs.avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia treatment) Study, Diabetic Medicines, 2006, vol. 23, No. 7, pp. 736-742.
Holman RR et al.,10-Year Follow-up of Intensive Glucose Control in Type 2 Diabetes,The New England Journal of Medicine, 2008, vol. 359, pp. 1577-1589.
Holman RR et al.A practical guide to Basal and Prandial Insulin therapy, Diabetic Medicine, 1985, vol. 2, pp. 45-53.
International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.
Inzucchi SE et al.Management of Hyperglycemia in Type 2 Diabetes: A Patient-Centered Approach: Position Statement of the American Diabetes Association (ADA) and the European Association for the Study of Diabetes (EASD),Diabetes care, 2012, vol. 35, pp. 1364-1379.
Iwamoto Yasuhi Ko et al: Insulin degludec in Japanese patients with type 1 diabetes mellitus: A randomized controlled trial,Journal of Diabetes Investigation,2013,vol. 4, No. 1, pp. 62-68.
Janka Hans U et al, Combination of oral antidiabetic agents with basal insulin; versus premixed insulin alone in randomized elderly patients with type 2 diabetes mellitus, Journal of the American Geriatrics Society, 2007,vol. 55, No. 2, pp. 182-188.
Kulzer B, et al. Effects of self-management training in type 2 diabetes: a randomized, prospective trial. Diabetic Medicine. 2007, vol. 24, No. 4, pp. 415-423.
LANTUS® (insulin glargine [rDNA origin] injection). sanofi-aventis U.S. LLC, Bridgewater, NJ, USA; 2007. Health Care Professional. Dosing & Titration. Available at: http://www.lantus.com/hcp/titration.aspx. Accessed Nov. 13, 2012.
Liebl A, et al. Direct costs and health-related resource utilisation in the 6 months after insulin initiation in German patients with type 2 diabetes mellitus in 2006: INSTIGATE study. Current Medical Research Opinion 2008,vol. 24, No. 3, pp. 2349-2358.
Meneghini L et al., The usage of a simplified self-titration dosing guideline (303 Algorithm) for insulin detemir in patients with type 2 diabetes-results of the randomized, controlled PREDICTIVE TM 303 study. Diabetes Obesity and Metabolism. 2007, vol. 9, pp. 902-913.
Nathan DM et al,Intensive Diabetes Treatment and Cardiovascular Disease in Patients with Type 1 Diabetes,The new england journal of medicine, 2005, vol. 353, No. 25, pp. 2643-2653.
Nathan DM et al.Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.
Nathan DM et al.The Effect of Intensive Treatment of Diabetes on the Development and Progression of Long-Term Complications in Insulin-Dependent Diabetes Mellitus,The Diabetes Control and Complications Trial Research Group,The New England Journal of medicine, 1993, vol. 329, No. 14, pp. 977-986.
Norris SL, et al. Self-management education for adults with type 2 diabetes: a meta-analysis on the effect of glycemic control. Diabetes Care, 2002, vol. 25, No. 7, pp. 1159-1171.
Ohkubo Y et al. Intensive insulin therapy prevents the progression of diabetic microvascular complications in Japanese patients with non-insulin-dependent diabetes mellitus: a randomized prospective 6-year study,Diabetes Research and Clinical Practice, 1995, vol. 28, No. 2 pp. 103-117.
Peyrot M, et al. Factors associated with injection omission/non-adherence in the Global Attitudes of Patients and Physicians in Insulin Therapy Study. Diabetes Obesity and Metabolism. 2012,vol. 14, pp. 1081-1087.
Peyrot M, et al.. Insulin adherence behaviours and barriers in the multinational Global Attitudes of Patients and Physicians in insulin therapy study. Diabetic Medcine. 2012,vol. 29, No. 5, pp. 682-689.
Philis-Tsimikas A et al.: Insulin degludec once-daily in type 2 diabetes:; Simple or step-wise titration (BEGIN: Once Simple Use), Advances in Therapy, 2013,vol. 30, No. 6, pp. 607-622.
Sakharova O V et al.Effects on post-prandial glucose and AGE precursors from two initial insulin strategies in patients with Type 2 diabetes uncontrolled by oral agents, Journal of Diabetes and Its Complications,2012,vol. 26, No. 4, pp. 333-338.
Schnell O, et al. Consensus statement on self-monitoring of blood glucose in diabetes. Diabetes, Stoffwechsel und Herz. 2009, vol. 4, pp. 285-289.
Selvin E et al,.Meta-Analysis: Glycosylated Hemoglobin and Cardiovascular Disease in; Diabetes Mellitus, Annals of internal medicine,2004, vol. 141, pp. 421-431.
The ADVANCE Collaborative Group, Patel A et al.Intensive Blood Glucose Control and Vascular Outcomes in Patients with Type 2 Diabetes, The new England Journal of Medicine, 2008, vol. 358, pp. 2560-2572.

(56) References Cited

OTHER PUBLICATIONS

UK Prospective Diabetes Study (UKPDS) Group, Intensive blood-glucose control with sulphonylureas or insulin compared with conventional treatment and risk of complications in patients with type 2 diabetes (UKPDS 33)., LANCET, 1998, vol. 352 (9131), pp. 837-853.
Yeaw J, et al. Cost of self-monitoring of blood glucose in Canada among patients on an insulin regimen for diabetes. Diabetes Therapeutics . Epub ,2012 vol. 3, No. 7, pp. 1-17 doi: 10.1007/s13300-012-0007-6.
Yeaw J, et al. Self-monitoring blood glucose test strip utilization in Canada. Diabetes. 2012;vol. 61(Suppl 1)p. A35.
Yeaw J, et al.. Cost of self-monitoring of blood glucose in the United States among patients on an insulin regimen for diabetes. Journal of Managed Care Pharmacy 2012, vol. 18, No. 1, pp. 21-32.
American Diabetes Association. Insulin administration. Diabetes Care. 2002 vol. 25: pp. S112-S115.
Heise T, et al.. Insulin degludec: four times lower pharmacodynamic variability than insulin glargine under steady-state conditions in type 1 diabetes. Diabetes Obesity and Metabolism , 2012, vol. 14, pp. 859-864.
Heise T, et al. Insulin degludec 200 U/mL is ultra-long-acting and has a flat and stable glucose-lowering effect. Diabetes.2012;, vol. 61(Suppl.1) p. A91.
Korsatko S, et al. Ultra-long-acting insulin degludec: bioequivalence and similar pharmacodynamics shown for two different formulations (U100 and U200). Diabetologia. 2011 , vol. 54(Suppl. 1) p. S427.
World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.
International Conference on Harmonisation. ICH Harmonised Tripartite Guideline:Guideline for Good Clinical Practice. E6 (R1), Step 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.
Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.
Garg S, et al. Preference for a new prefilled insulin pen compared with the original pen. Current Medical Research & Opinion. 2011 vol. 27 pp. 2323-2333.
Garber AJ, et al; on behalf of the NN1250-3582 BEGINTM BB T2D trial investigators. Insulin degludec, an ultra-long acting basal insulin, versus insulin glargine in basal-bolus treatment with mealtime insulin aspart in type 2 diabetes (BEGINTM Basal-Bolus Type 2): a phase 3, randomised, open-label, treat-to-target non-inferiority trial. Lancet.2012, vol. 379, pp. 1498-1507.
Zinman B, et al; on behalf of the NN1250-3579 BEGIN tm Once Long trial investigators. Insulin degludec versus insulin glargine in insulin-naïve patients with type 2 diabetes: a 1-year, randomized, treat-to-target trial (BEGIN tm Once Long). Diabetes Care. 2012 vol. 35 pp. 2464-2471.
Springer et al., "Management of Type 2 Diabetes Mellitus in Children and Adolescents", Pediatrics, 2013, vol. 131, No. 2, pp. e648-e664.
Heise et al., "Ultra-Long-Acting Insulin Degludec has a Flat and Stable Glucose-Lowering Effect in Type 2 Diabetes," Diabetes, Obesity and Metabolism, 2012, vol. 14, pp. 944-950.
Heller et al., "Insulin Degludec, an Ultra-Longacting Basal Insulin, Versus Insulin Glargine . . . : a Phase 3, Randomized, Open-Label, Treat-to-Target Non-Inferiority Trial," The Lancet, 2012, vol. 379, pp. 1489-1497.
Bergenstal R, Bhargava A, Jain RK, et al; on behalf of the NN1250-3672 BEGIN TM Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.
Onishi Y, et al. Superior glycaemic control with once daily insulin degludec/ insulin aspart versus insulin glargine in Japanese adults with type 2 diabetes inadequately controlled on oral drugs: a randomized, controlled phase 3 trial. Diabetes Obesity and Metabolism. 2013 vol. 15, pp. 826-832.
Rakel RE. Improving patient acceptance and adherence in diabetes management: a focus on insulin therapy. Advances in Therapy. 2009, vol. 26 pp. 838-846.
Ross SA, et al. Barriers to effective insulin treatment: the persistence of poor glycemic control in type 2 diabetes. Current Medical Research and Opinion 2011, vol. 27(Suppl 3), pp. 13-20.
Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.
Rubin RR et al.. Factors affecting use of insulin pens by patients with type 2 diabetes. Diabetes Care. 2008 vol. 31 pp. 430-432.
Peyrot M and Rubin RR. Factors associated with persistence and resumption of insulin pen use for patients with type 2 diabetes. Diabetes Technology & Therapeutics. 2011 vol. 13 No. 43-48.
Oyer D,et al. Ease of use and preference of a new versus widely available pre-filled insulin pen assessed by people with diabetes, physicians and nurses. Expert Opinion on Drug Delivery. 2011 vol. 8, pp. 1259-1269.
Bailey T,et al Usability and preference evaluation of a prefilled insulin pen with a novel injection mechanism by people with diabetes and healthcare professionals. Current Medical Research and Opinion 2011, vol. 27 pp. 2043-2052.
Nadeau DA,et al. Healthcare professional and patient assessment of a new prefilled insulin pen versus two widely available prefilled insulin pens for ease of use, teaching and learning. Current Medical Research and Opinion 2012;vol. 28.No. 1 pp. 3-13.
Lajara R, et al. Healthcare professional and patient perceptions of a new prefilled insulin pen versus vial and syringe. Expert Opinion on Drug Delivery 2012, vol. 9, pp. 1181-1196.
Bailey T, et al. FlexTouch® for the delivery of insulin: technical attributes and perception among patients and healthcare professionals. Expert Review of Medical Devices 2012, vol. 9, pp. 209-217.
Talboys Catalog, 2008 Laboratory Equipment Catalog, Talboys by Troemner, 122 pages (2008).
Heise et al "Lower Within-Subject Variability of Insulin Detemir in Comparison to NPH Insulin an Insulin Glargine in People with Type 1 Diabetes" Diabetes, 2004, vol. 53, pp. 1614-1620.
Novo Nordisk, Levemir Product Information, Jun. 16, 2005. 42 pages.
"America Pink", http://america.pink/insulin-degludec_2091149.html, downloaded Aug. 24, 2016.
L. Heinemann and J. H. Anderson Jr. Diabetes Technol Ther 6 (5):698-728, 2004.
Living with Diabetes, available at http://www.diabetes.org/living-with-diabetes/treatment-and-care/medication/?loc=lwd-slabnav, accessed on Jan. 5, 2017.
WebMD "What is a unit of insulin," available at http://answers.webmd.com/answers/1196453/what-is-a-unit-of-insulin.
Heise et al., "Insulin Degludec 200 U/mL is Ultra-Long Acting and Has a Flat and Stable Glucose-Lowering Effect," Canadian Journal of Diabetes, 2012, vol. 36, No. 6, p. S13.
Anthony H. Barnett, Diabetic Medicine, A Review of Basal Insulins, 2003, vol. 20, No. 11, pp. 873-885.
Heise, T. et al., Diabetes, Obesity and Metabolism, Towards Peakless, Reproducible and Long-Acting Insulins. An Assessment of the Basal Analogues Based on Isoglycaemic Clamp Studies, 2007, vol. 9, No. 5, pp. 648-659.
IDF Clinical Guidelines Task Force, Brussels: International Diabetes Federation 2005, Global Guideline for Type 2 Diabetes, 2005.
IDF Clinical Guidelines Task Force, Brussels: International Diabetes Federation 2007, Guideline for Management of Postmeal Glucose, 2007.

(56) References Cited

OTHER PUBLICATIONS

Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.
Havelund, S. et al, "The Mechanism of Protraction of Insulin Detemir, a Long-Acting, Acylated Analog of Human Insulin", Pharmaceutical Research, 2004, vol. 21, No. 8, pp. 1498-1504.
Barnett, A.H., "A Review of Basal Insulins," Diabet Med, 2003, vol. 20, No. 11, pp. 873-885.
Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.
Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.
Definition of Moiety From http://dictionary.reference.com/browse/moiety, 2010, pp. 1-3.
Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.
Schlichtkrull, J., "Insulin Crystals", Acta Chemica Scandinavica, 1956, vol. 10, No. 9, pp. 1455-1458.
Vajo et al., "Genetically Engineered Insulin Analogs: Diabetes in the New Millennium," Pharma Rev, 2000, vol. 52, No. 1, pp. 1-9.
Whittingham, J.L. et al., "Crystallographic and Solution Studies of N-Lithocholyl Insulin: A New Generation of prolonged-Acting Human Insulins", Biochemistry, 2004, vol. 42, pp. 5987-5995.
Brange, J et al Diabetic Medicine Neutral Insulin Solutions Physically Stabilized by Addition of Zn2+, 1986, vol. 3, No. 6, pp. 532-536.
Jonassen, I. et al., Pharmaceutical Research 2006, vol. 23, No. 1, pp. 49-55.
Annual Review Endocrine Metabolism 2000, pp. 46-53.
Nathan, D. M. et al., "Management of Hyperglycemia in Type 2 Diabetes: A Consensus Algorithm for the Initiation and Adjustment of Therapy," Diabetes Care, 2008, vol. 31, No. 1, pp. 173-175.
Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.
Hinds et al., "PEGylated insulin in PLGA microparticles. In vivo and in vitro analysis," Journal of Controlled Release, 2005, vol. 104, No. 3, pp. 447-460.
Heller. S R, Current Medical Research and Opinion, "Insulin Analogues", 2002, vol. 18, No. 1, pp. 40-47.
I. Jonassen et al., Diabetologia, "Insulin Degludec: Multi-Hexamer Formation Is the Underlying Basis for This New Generation Ultra-Long Acting Basal Insulin", 2010, vol. 53, No. 1, pp. S388.
R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", 2010, vol. 53, No. 1, pp. S389.
Samuel et al. "Studies on the immunogenicity of protamines in humans and experimental animals by means of a micro-complement fixation test." Clin. Exp. Immunol. vol. 33: pp. 252-260. 1978.
Kurtz et al. "Circulating IgG antibody to protamine in patients treated with protamine-insulins." Diabetologica. vol. 25: pp. 322-324. 1983.
Definition of Moiety From http://dictionary.reference.com/browse/moiety, Aug. 26, 2010, pp. 1-3.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, 2010, vol. 53, No. 1, pp. S389.
I. Jonassen et al., "Insulin Degludec: Multi-Hexamer Formation Is the Underlying Basis for This New Generation Ultra-Long Acting Basal Insulin", Diabetologia, 2010, vol. 53, No. 1, pp. S388.

I. Jonassen et al., "Insulin Degludec: Multi-Hexamer Formation Is the Underlying Basis for This New Generation Ultra-Long Acting Basal Insulin", Diabetologia, Sep. 2010, vol. 53, No. 1, pp. S388.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, Sep. 2010, vol. 53, No. 1, pp. S389.
Lane W. S. et al., High-dose insulin therapy: is it time for U-500 insulin?, Endocrine Practice, 2009, vol. 15, No. 1, pp. 71-79.
Segal A. R. et al., Use of concentrated insulin human regular (U-500) for patients with diabetes, American Journal of Health-System Pharmacy, 2010, vol. 67, No. 18, pp. 1526-1535.
Valentine V., Don't Resist Using U-500 Insulin and Pramlintide for Severe Insulin Resistance, Clinical Diabetes, 2012, vol. 30, No. 2, pp. 80-84.
Obesity Society: Your weight and diabetes—http://www.obesity.org/resources-for/your-weight-and-diabetes.htm, (accessed Jul. 21, 2015).
Inzucchi S. E. et al., Management of hyperglycaemia in type 2 diabetes: a patient-centered approach. Position statement of the American Diabetes Association (ADA) and the European Association for the Study of Diabetes (EASD), Diabetologia, 2012, vol. 55, No. 6, pp. 1577-1596.
Crasto W et al., Insulin U-500 in severe insulin resistance in type 2 diabetes mellitus, Postgraduate Medical Journal, 2009, vol. 85, No. 1002, pp. 219-222.
Heise T et al., Insulin Degludec Has a Two-Fold Longer Half-Life and a More Consistent Pharmacokinetic Profile Than Insulin Glargine, Diabetes, 2011, vol. 60(Suppl 1), LB11, (Abstract 37-LB).
Nosek L. et al., Ultra-Long-Acting Insulin Degludec Has a Flat and Stable Glucose-Lowering Effect, Diabetes 2011, 60(Suppl 1), LB14 (Abstract 49-LB).
Korsatko S. et al., Ultra-Long-Acting Insulin Degludec: Two Different Formulations (U100 and U200) Are Bioequivalent and Show Similar Pharmacodynamics, Diabetes 2011, 60(Suppl 1), A624 (Abstract 2349-PO).
Zinman B. et al., Insulin degludec, an ultra-long-acting basal insulin, once a day or three times a week versus insulin glargine once a day in patients with type 2 diabetes: a 16-week, randomized, open-label, phase 2 trial. The Lancet, 2011, vol. 377, 924-931.
Heller S. et al., Insulin degludec, an ultra-longacting basal insulin, versus insulin glargine in basal-bolus treatment with mealtime insulin aspart in type 1 diabetes (BEGIN Basal-Bolus Type 1): a phase 3, randomised, open-label, treat-to-target non-inferiority trial, The Lancet 2012, vol. 379, pp. 1489-1497.
Garber A. J. et al., Insulin degludec, an ultra-longacting basal insulin, versus insulin glargine in basal-bolus treatment with mealtime insulin aspart in type 2 diabetes (BEGIN Basal-Bolus Type 2): a phase 3, randomised, open-label, treat-to-target non-inferiority trial, The Lancet, 2012, vol. 379, pp. 1498-1507.
Declaration of Helsinki, Ethical principles for medical research involving human subjects., Journal of Indian Medical Association, 2009, vol. 107, No. 6, pp. 403-405.
Defining and Reporting Hypoglycemia in Diabetes: A report from the American Diabetes Association Workgroup on Hypoglycemia, Diabetes Care, 2005, vol. 28, No. 5, pp. 1245-1249.
HUMULIN® R Regular U-500 (Concentrated), Insulin Human Injection, USP (rDNA Origin), Eli Lilly and Company, Lilly USA, LLC, Indianapolis, IN 46285, USA, 1996.
Thornton S. et al., Intravenous overdose of insulin glargine without prolonged hypoglycemic effects, The Journal of Emergency Medicine, 2012, vol. 43, No. 3, pp. 435-437, XP002711646.
Zinman B. et al., Insulin degludec versus insulin glargine in insulin-naive patients with type 2 diabetes: a 1-year, randomized, treat-to-target trial (BEGIN Once long), Diabetes Care, 2012, vol. 35, No. 12, pp. 2464-2471, XP9172018.
Rodbard H et al., Reduced risk of hypoglycaemia with insulin degludec vs insulin glargine in patients with type 2 diabetes requiring high doses of basal insulin: meta-analysis of five randomized trials. Presented as an oral at the AACE 21st Annual Scientific and Clinical Congress, Philadelphia, PA, 2012, (Abstract 241).

(56) References Cited

OTHER PUBLICATIONS

ICH Harmonised Tripartite Guideline: Guideline for Good Clinical Practice, Journal of postgraduate medicine, 2001, vol. 47, No. 3, pp. 199-203.
Marcus A., Diabetes care—insulin delivery in a changing world, The Medscape Journal of Medicine, 2008, vol. 10, No. 5, 120.

METHOD OF TREATING DIABETES MELLITUS BY ADMINISTRATION, AT SPECIFICALLY DEFINED INTERVALS, OF A DERIVATIVE OF A NATURALLY OCCURRING INSULIN OR INSULIN ANALOGUE, THE DERIVATIVE HAVING A PROLONGED PROFILE OF ACTION

FIELD OF THE INVENTION

The present invention relates to a novel insulin administration scheme, which is i.a. useful in treatment of diabetes mellitus and hyperglycaemia, in particular of insulin-dependent diabetes mellitus. The administration of insulin and insulin involves use of analogues having a prolonged profile of action in a novel dosage regimen.

BACKGROUND OF THE INVENTION

Diabetes mellitus often requires insulin treatment to establish proper metabolic control (comprising mainly glycaemic control, but also other metabolic parameters benefit from insulin treatment). The established practise of insulin treatment is to administer the insulin product once or more often per day, optionally in combination with other treatment modalities, as described in available treatment guidelines. Intravenous and subcutaneous insulin infusion is also used in clinical practise.

One widely used insulin treatment option is to administer a long acting insulin product, also referred to as basal insulin, to cover the insulin need of the patient wholly or partially. The long acting insulin is administered once or more often per day, at the same time every day, and is used on both type 1 diabetes and type 2 diabetes as well as for other forms of insulin requiring disease states (hyperglycaemia of any cause).

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin, given at the same time every day, to cover the basal insulin requirement supplemented by bolus injections of a rapid acting insulin to cover the insulin requirement related to meals.

The current practice in management of diabetes and hyperglycaemia is set forth in e.g.:

IDF Clinical Guidelines Task Force. Global Guideline for Type 2 Diabetes. *Brussels: International Diabetes Federation*, 2005, http://www.idf.org/webdata/docs/IDF %20GGT2D.pdf.

IDF Clinical Guidelines Task Force. Guideline for Management of PostMeal Glucose. *Brussels: International Diabetes Federation*, 2007, http://www.idf.org/webdata/docs/Guideline_PMG_final.pdf, D. M. Nathan, J. B. Buse, M. B. Davidson, E. Ferrannini, R. R. Holman, R. Sherwin, and B. Zinman. Management of hyperglycemia in type 2 diabetes: a consensus algorithm for the initiation and adjustment of therapy: update regarding thiazolidinediones: a consensus statement from the American Diabetes Association and the European Association for the Study of Diabetes. *Diabetes care* 31 (1):173-175, 2008.

Reviews relating to basal insulin analogues and their characteristics and current clinical use can i.a. be found in: T. Heise and T. R. Pieber. Towards peakless, reproducible and long-acting insulins. An assessment of the basal analogues based on isoglycaemic clamp studies. *Diabetes Obes Metab* 9 (5):648-659, 2007, and A. H. Barnett. A review of basal insulins. *Diabet Med* 20 (11):873-885, 2003.

DESCRIPTION OF THE INVENTION

Figure 1:
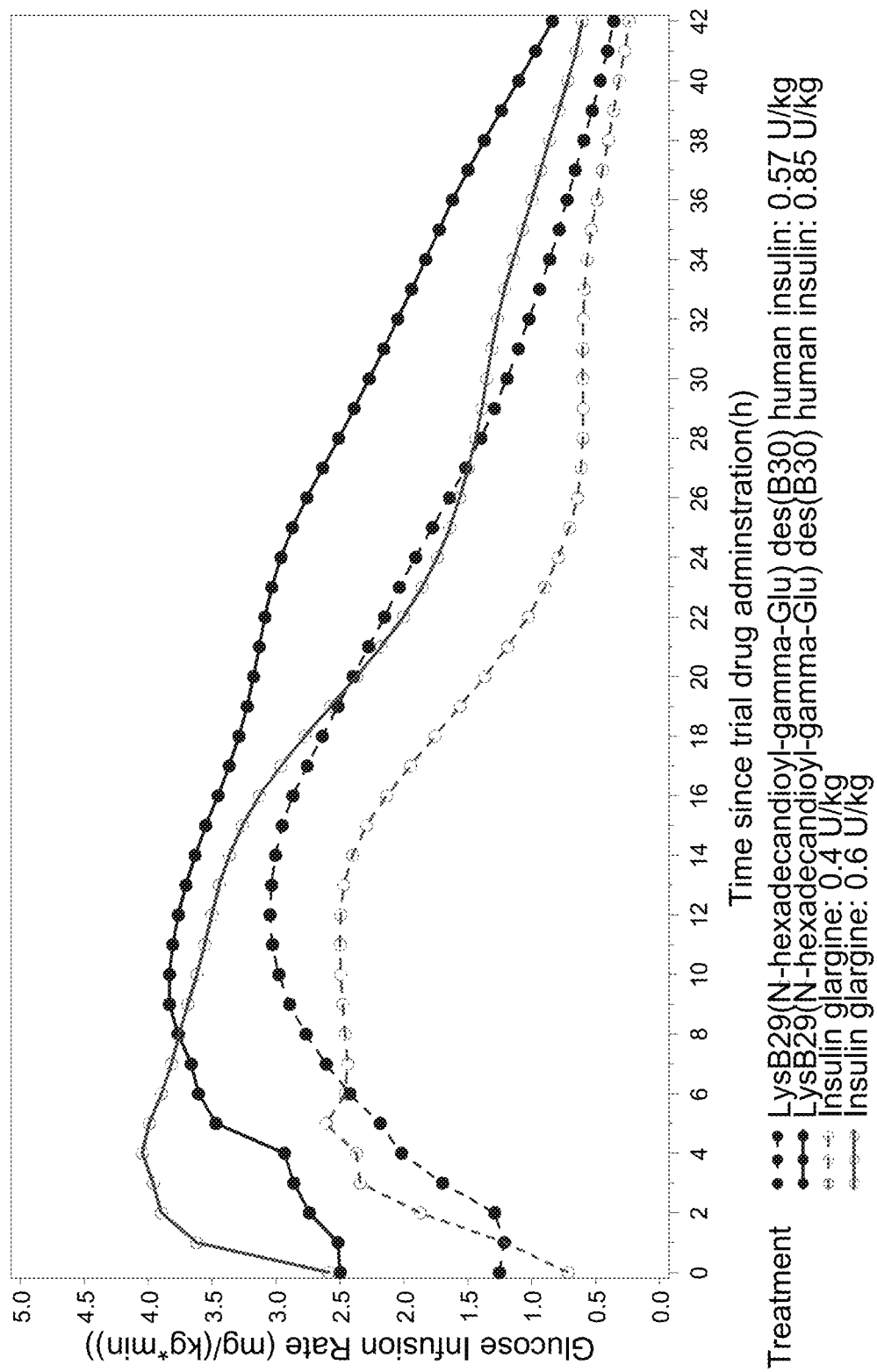
FIG. 1 shows the glucose infusion rate plotted against the time since the administration of the trial drug.

The present invention is based on the surprising finding that it is possible to treat a condition or disease where administration of insulin will be of benefit, such as diabetes or hyperglycaemia, by administration of insulin at intervals of varying length. For instance it has been verified that intervals of administration varying from as little as 8 hours and up to 40 hours using a dosage which at regular intervals would have been administered at 24 hour intervals provide for satisfactory diabetes treatment regimens. A number of advantages directly follow from such flexible treatment regimens:

Convenience is improved for patients by the possibility for flexible administration. For example patients can adapt the administration to their life style rather than being dependent on dosage at fixed time points, which can be advantageous in cases of incompliance or distraction where a dose is administered earlier or later than the intended time of injection; if the patient is, e.g., travelling, a child or a teenager, doing sports or a shift worker; or for any other reason has an irregular lifestyle or for whom irregularities in daily routines occur or cannot be avoided. Another example where flexible administration is advantageous is if the patient lives in a nursing home or if the patient is otherwise dependent on assisted administration of insulin. Improved convenience potentially improves patient compliance ultimately improving the long term outcome for the patient.

In one embodiment the method of the present invention enables use of flexible intervals of administration, i.e. administration intervals of varying length, without compromising the glycaemic control or safety profile. An indication of the glycaemic control, such as the blood glucose or the level of HbA1c, may be determined as shown in Example 2, 3 or Example 4. An indication of the safety profile may be determined as shown in Example 2, 3 or Example 4.

In one embodiment the invention hence relates to a method for treatment of a condition or disease where administration of insulin will be of benefit, comprising administering, to a patient in need thereof, effective dosages of an insulin derivative of a naturally occurring insulin or an insulin analogue, wherein said insulin exhibits a prolonged profile of action and wherein said dosages are administered at intervals which are of varying length.

The invention also relates to use of such insulin derivatives in treatment methods discussed herein, and the invention also relates to use of such insulin derivatives in preparation of pharmaceutical compositions for the treatment of the diseases and conditions discussed herein.

Diseases and conditions which are the primary targets for this method are diabetes mellitus (type 1 or 2) or other conditions characterized by hyperglycaemia, but also metabolic diseases and conditions in general where the metabolic effects of insulin has a clinical relevance are of interest, such as pre-diabetes, impaired glucose tolerance, metabolic syndrome, obesity, cachexia, in vivo beta-cell loss/death, excessive appetite, and inflammation. All these types of conditions are known to or believed to benefit from a stable metabolic state in the subject who has the disease/condition.

Accordingly, any therapeutic regimen where administration of insulin is included may be modified by implementing the current teachings, meaning that such therapies will include administration of prolonged profile of action insulins, insulin analogues or derivatives of either of these according to the teachings provided herein.

Treatment Regimens of the Invention

The invention is best used at the convenience of the patient. Therefore, administration intervals will be explored for each insulin product exhibiting a sufficiently long profile of action to allow for the presently disclosed dosage regimens. The final mode of use thus depends both on the product's capabilities and on the disposition and preference of the patient. This is due to the fact that the effect of any insulin depends on the insulin need of the individual patient and the sensitivity to the pharmacodynamic actions of insulin and lastly also to the preferences of the patient in a given situation. These conditions may change over time, both in terms of longer periods (years) and from day to day. From a pharmacological perspective optimal dosing intervals could be defined be the intervals giving rise to the least variation in the blood concentration levels of a particular insulin product thus giving rise to the optimal consistency in effect. Invariably, such an approach will point to the use of fixed intervals between doses. The theoretical basis for the current invention is that for insulins covered by this invention the variation introduced by changing dosing intervals during treatment is negligible compared to other factors affecting the variability in safety and efficacy of such insulins.

Nevertheless, the present invention provides a number of embodiments of a general dosage regimen. Although an intended or optimal interval of administration of same length has been identified the present invention provides the possibility of using intervals of dosage administration of varying length.

Due to the flexible administration intervals between dosages will be of varying length and therefore the intervals are described herein as the arithmetic mean of the intervals. The expression "arithmetic mean" as used herein designates the sum of the $a_i$'s divided by n, where n numbers are given and each number is denoted by $a_i$, where i=1, . . . , n. In one embodiment the mean of the intervals is determined over a period of at least 4 days, such as over a period of at least 1 week or over a period of at least 2 weeks. In one embodiment the mean of the intervals is determined over a period of at least 3 weeks, such as over a period of 6 weeks or over a period of 12 weeks. In one embodiment the mean of the intervals is determined over a period of at least 20 weeks, such as over a period of 26 weeks or over a period of 32 weeks.

In one embodiment no more than 4, such as no more than 3 or no more than 2, intervals which are adjacent to each other are no more than 0.9 times the mean of said intervals. In one embodiment no more than 4, such as no more than 3 or no more than 2, intervals which are adjacent to each other are at least than 1.1 times the mean of said intervals.

In one embodiment the invention relates to a method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein at least one of said intervals has a length of
   a. at least 1.04 times the mean of said intervals, or
   b. no more than 0.96 times the mean of said intervals.

In one embodiment the insulin for use in the present invention is an insulin analogue or a derivative thereof.

In one embodiment the invention relates to a method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein
   a. at least one of said intervals has a length of
      i. at least 1.04 times the mean of said intervals, or
      ii. no more than 0.96 times the mean of said intervals; and
   b. said intervals are not selected from the group consisting of
      i. administration at 3 fixed weekdays, such as Monday-Wednesday-Friday; Monday-Wednesday-Saturday; Monday-Thursday-Saturday; Tuesday-Thursday-Saturday; Tuesday-Thursday-Sunday; and Tuesday-Friday-Sunday; or
      ii. administration at 2 fixed weekdays, such as Monday-Thursday; Monday-Friday; Tuesday-Friday; Tuesday-Saturday; Wednesday-Saturday; Wednesday-Sunday; and Thursday-Sunday.

In one embodiment the invention relates to a method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein the mean of said intervals is less than 56 hours and at least one of said intervals is
   a. at least 1.04 times the mean of said intervals, or
   b. no more than 0.96 times the mean of said intervals.

In one embodiment the invention relates to a method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein at least one of said intervals has a length of
   a. at least 1.3 times the mean of said intervals, or
   b. no more than 0.85 times the mean of said intervals.

In one embodiment at least two, such as at least three or at least four, of said intervals have a length of a) at least 1.04 times the mean of said intervals, or b) no more than 0.96 times the mean of said intervals. In one embodiment at least five, such as at least ten or at least twenty, of said intervals have a length of a) at least 1.04 times the mean of said intervals, or b) no more than 0.96 times the mean of said intervals. In one embodiment at least $\frac{1}{1000}$, such as at least $\frac{1}{500}$ or at least $\frac{1}{300}$, of said intervals have a length of a) at least 1.04 times the mean of said intervals, or b) no more than 0.96 times the mean of said intervals. In one embodiment at least $\frac{1}{200}$, such as at least $\frac{1}{100}$ or at least $\frac{1}{50}$, of said intervals have a length of a) at least 1.04 times the mean of said intervals, or b) no more 0.96 times the mean of said intervals. In one embodiment at least 1/40, such as at least 1/30 or at least 1/20, of said intervals have a length of a) at least 1.04 times the mean of said intervals, or b) no more than 0.96 times the mean of said intervals. In one embodiment at least 1/15, such as at least 1/10 or at least 1/5, of said intervals have a length of a) at least 1.04 times the mean of said intervals, or b) no more than 0.96 times the mean of said intervals. In one embodiment at least 1/3, such as at least 1/2 or all, of said intervals have a length of a) at least 1.04 times the mean of said intervals, or b) no more than 0.96 times the mean of said intervals.

In one embodiment the dosage is not adjusted between administrations. In one embodiment the dosage is substantially the same at every administration.

In one embodiment said intervals occur over a period of at least 3 weeks, such as at least 10 weeks or at least 26 weeks. In one embodiment said intervals occur over a period of 3 weeks, such as over a period of 10 weeks or over a period of 26 weeks.

In one embodiment at least one of said intervals is at least the mean of said intervals plus 1/24 times the mean of said intervals. In one embodiment at least one of said intervals is at least the mean of said intervals plus 1.5/24 times the mean of said intervals. In one embodiment at least one of said intervals is at least the mean of said intervals plus 2/24 times the mean of said intervals. In one embodiment at least one of said intervals is at least the mean of said intervals plus 2.5/24 times the mean of said intervals. In one embodiment at least one of said intervals is at least the mean of said intervals plus 3/24 times the mean of said intervals. In one embodiment at least one of said intervals is at least the mean of said intervals plus 3.5/24 times the mean of said intervals. In one embodiment at least one of said intervals is at least the mean of said intervals plus 4/24 times the mean of said intervals. In one embodiment at least one of said intervals is at least the mean of said intervals plus 5/24 times the mean of said intervals.

In one embodiment at least one of said intervals is no more than the mean of said intervals minus 1/24 times the mean of said intervals. In one embodiment at least one of said intervals is no more than the mean of said intervals minus 1.5/24 times the mean of said intervals. In one embodiment at least one of said intervals is no more than the mean of said intervals minus 2/24 times the mean of said intervals. In one embodiment at least one of said intervals is no more than the mean of said intervals minus 2.5/24 times the mean of said intervals. In one embodiment at least one of said intervals is no more than the mean of said intervals minus 3/24 times the mean of said intervals. In one embodiment at least one of said intervals is no more than the mean of said intervals minus 3.5/24 times the mean of said intervals. In one embodiment at least one of said intervals is no more than the mean of said intervals minus 4/24 times the mean of said intervals. In one embodiment at least one of said intervals is no more than the mean of said intervals minus 5/24 times the mean of said intervals.

In one embodiment at least one of said intervals is at least 1.1 times, such as at least 1.15 times, the mean of said intervals. In one embodiment at least one of said intervals is at least 1.2 times, such as at least 1.25 times, the mean of said intervals. In one embodiment at least one of said intervals is at least 1.3 times, such as at least 1.35 times, the mean of said intervals. In one embodiment at least one of said intervals is at least 1.4 times the mean of said intervals. In one embodiment at least one of said intervals is at least 1.45 times the mean of said intervals. In one embodiment at least one of said intervals is at least 1.5 times the mean of said intervals. In one embodiment at least one of said intervals is at least 1.55 times the mean of said intervals. In one embodiment at least one of said intervals is at least 1.6 times the mean of said intervals. In one embodiment at least one of said intervals is at least 1.65 times the mean of said intervals. In one embodiment at least one of said intervals is at least 1.7 times the mean of said intervals. In one embodiment at least one of said intervals is at least 1.75 times the mean of said intervals.

In one embodiment at least one of said intervals is no more than 0.95 times the mean of said intervals. In one embodiment at least one of said intervals is no more than 0.90 times the mean of said intervals. In one embodiment at least one of said intervals is no more than 0.85 times the mean of said intervals. In one embodiment at least one of said intervals is no more than 0.80 times the mean of said intervals. In one embodiment at least one of said intervals is no more than 0.75 times the mean of said intervals. In one embodiment at least one of said intervals is no more than 0.70 times the mean of said intervals. In one embodiment at least one of said intervals is no more than 0.65 times the mean of said intervals. In one embodiment at least one of said intervals is no more than 0.60 times the mean of said intervals. In one embodiment at least one of said intervals is no more than 0.55 times the mean of said intervals. In one embodiment at least one of said intervals is no more than 0.50 times the mean of said intervals. In one embodiment at least one of said intervals is no more than 0.45 times the mean of said intervals. In one embodiment at least one of said intervals is no more than 0.40 times the mean of said intervals. In one embodiment at least one of said intervals is no more than 0.35 times the mean of said intervals. In one embodiment at least one of said intervals is no more than 0.30 times the mean of said intervals.

In one embodiment the mean of said intervals is less than 54 hours, such as less than 52 hours or less than 50 hours. In one embodiment the mean of said intervals is less than 48 hours, such as less than 42 hours or less than 36 hours. In one embodiment the mean of said intervals is less than 30 hours, such as less than 24 hours or less than 18 hours. In one embodiment the mean of said intervals is at least 8 hours, such at least 12 hours or at least 16 hours. In one embodiment the mean of said intervals is at least 20 hours, such as at least 24 hours or at least 28 hours.

In one embodiment the mean of said intervals is at least 12 hours, such as at least 16 hours or at least 20 hours. In one embodiment the mean of said intervals is at least 24 hours. In one embodiment the mean of said intervals is at least 28 hours, such as at least 32 hours or at least 36 hours. In one embodiment the mean of said intervals is at least 48 hours, such as at least 72 hours or at least 96 hours. In one embodiment the mean of said intervals is at least 120 hours, such as at least 144 hours or at least 168 hours. In one embodiment the mean of said intervals is at least 182 hours, such as at least 206 hours or at least 230 hours.

In one embodiment said dosages are administered every day or every second day.

In one embodiment at least one of said intervals is between 8 and 22 hours, such as between 8 and 20 hours or between 8 and 18 hours. In one embodiment at least one of said intervals is between 8 and 16 hours, such as between 8 and 14 hours or between 8 and 12 hours. In one embodiment at least one of said intervals is between 26 and 40 hours, such as between 28 and 40 hours or between 30 and 40 hours. In one embodiment at least one of said intervals is between 32 and 40 hours, such as between 34 and 40 hours or between 36 and 40 hours.

In one embodiment at least one of said intervals is between 4 and 11 hours, such as between 4 and 10 hours or between 4 and 9 hours. In one embodiment at least one of said intervals is between 4 and 8 hours, such as between 4 and 7 hours or between 4 and 6 hours. In one embodiment at least one of said intervals is between 13 and 20 hours, such as between 14 and 20 hours or between 15 and 20 hours. In one embodiment at least one of said intervals is between 16 and 20 hours, such as between 17 and 20 hours or between 18 and 20 hours. In one embodiment at least one of said intervals is between 16 and 22 hours, such as between 16 and 20 hours or between 16 and 18 hours.

In one embodiment at least one of said intervals is between 16 and 16 hours, such as between 16 and 14 hours or between 16 and 12 hours. In one embodiment at least one of said intervals is between 52 and 80 hours, such as between 56 and 80 hours or between 60 and 80 hours. In one embodiment at least one of said intervals is between 64 and 80 hours, such as between 68 and 80 hours or between 72 and 80 hours.

The method according to any one of the embodiments herein, wherein substantially no other naturally occurring insulin, insulin analogue or derivative of naturally occurring insulin or insulin analogue is administered to said patient.

Insulins with Prolonged Action Useful in the Invention

In one embodiment the insulins, insulin analogues or derivatives used in the present invention has a prolonged profile of action. In one embodiment "prolonged profile of action" is defined as a half-life of at least 18 hours, such as at least 24 hours, wherein the half-life may be determined as described in Example 1 herein. In one embodiment "prolonged profile of action" is defined as a half-life of at least 12 hours, such as at least 12 hours and less than 24 hours, wherein the half-life may be determined as described in Example 1 herein.

In one embodiment the insulins, insulin analogues or derivatives used in the present invention has 1) a sufficiently prolonged profile of action in most subjects to cover the injection intervals used and optionally 2) a relatively flat and stable shape of the activity profile in order not to cause undue increase in insulin action when used with a short dosing interval. An indication of the duration of action in clinical use may be obtained under experimental conditions, the euglycaemic glucose clamp procedure (L. Heinemann and J. H. Anderson-Jr. Measurement of insulin absorption and insulin action. *Diabetes Technol Ther* 6 (5):698-718, 2004), cf. Example 1. An indication of the flatness of the activity profile in clinical use may be obtained under experimental conditions as described in Example 1 or Example 2. An indication of the stability of the activity profile in clinical use may be obtained under experimental conditions as described in Example 1 or Example 2.

In one embodiment the naturally occurring insulin, an insulin analogue or a derivative of a naturally occurring insulin or of an insulin analogue does not have a relatively high peak activity profile. This peak is defined as the maximum in a curve when glucose infusion is plotted against time since administration of the drug. An indication of the peak of the activity profile in clinical use may be obtained under experimental conditions as described in Example 1 or Example 2.

Interesting derivatives with prolonged profiles of action are disclosed in WO 2005/012347 (Novo Nordisk) and these are all considered especially useful for putting the present invention into practice—in the following, these are termed "the '347 derivatives".

In one embodiment the insulins, insulin analogues or derivatives is insulin determir. In one embodiment the insulins, insulin analogues or derivatives is insulin glargine.

By "Insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues The insulin analogues may be such wherein position 28 of the B chain may be modified from the natural Pro residue to one of Asp, Lys, or Ile. In another embodiment Lys at position B29 is modified to Pro. In one embodiment B30 may be Lys and then B29 can be any codable amino acid except Cys, Met, Arg and Lys.

Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

With "desB30 Insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The expression "a codable amino acid" or "a codable amino acid residue" is used to indicate an amino acid or amino acid residue which can be coded for by a triplet ("codon") of nucleotides.

hGlu is homoglutamic acid.

α-Asp is the L-form of —HNCH(CO—)CH$_2$COOH.
β-Asp is the L-form of —HNCH(COOH)CH$_2$CO—.
α-Glu is the L-form of —HNCH(CO—)CH$_2$CH$_2$COOH.
γ-Glu is the L-form of —HNCH(COOH)CH$_2$CH$_2$CO—.
α-hGlu is the L-form of —HNCH(CO—)CH$_2$CH$_2$CH$_2$COOH.
δ-hGlu is the L-form of —HNCH(COOH)CH$_2$CH$_2$CH$_2$CO—.
β-Ala is —NH—CH$_2$—CH$_2$—COOH.
Sar is sarcosine (N-methylglycine).

The expression "an amino acid residue having a carboxylic acid group in the side chain" designates amino acid residues like Asp, Glu and hGlu. The amino adds can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

When an insulin derivative according to the invention is stated to be "soluble at physiological pH values" it means that the insulin derivative can be used for preparing injectable insulin compositions that are fully dissolved at physiological pH values. Such favourable solubility may either be due to the inherent properties of the insulin derivative alone or a result of a favourable interaction between the insulin derivative and one or more ingredients contained in the vehicle.

The following abbreviations have been used in the specification and examples:
IDA: Iminodiacetic acid,
Sar: Sarcosine (N-methyl-glycine),
Su: succinimidyl=2,5-dioxo-pyrrolidin-1-yl.

Use of '347 Derivative in the Method of the invention

The method of the invention include embodiments where the derivative is a '347 derivative, i.e. a derivative of a naturally occurring insulin or an insulin analogue has a side chain attached either to the α-amino group of the N-terminal amino acid residue of the B chain or to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with the α-amino group of the N-terminal amino add residue of the B chain or together with the ε-amino group of a Lys residue present in the B chain of the parent insulin;
a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to the α-amino group of the N-terminal amino acid residue of the B chain or to the ε-amino group of a Lys residue present in the B chain of the parent insulin;

X is:
—CO—;
—COCH(COOH)$\underline{C}$O—;
—CON(CH$_2$COOH)CH$_2$$\underline{C}$O—;
—CON(CH$_2$COOH)CH$_2$CON(CH$_2$COOH)CH$_2$$\underline{C}$O—;
—CON(CH$_2$CH$_2$COOH)CH$_2$CH$_2$$\underline{C}$O—;
—CON(CH$_2$CH$_2$COOH)CH$_2$CH$_2$CON(CH$_2$CH$_2$COOH)CH$_2$CH$_2$$\underline{C}$O—;
—CONHCH(COOH)(CH$_2$)$_4$NH$\underline{C}$O—;
—CON(CH$_2$CH$_2$COOH)CH$_2$$\underline{C}$O—; or
—CON(CH$_2$COOH)CH$_2$CH$_2$$\underline{C}$O—.

that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof, provided that when W is a covalent bond and X is —CO—, then Z is different from —COOH.

In one embodiment the side chain —W—X—Y—Z is attached to the α-amino group of the N-terminal amino acid residue of the B chain of the parent insulin.

In another embodiment of the invention, side chain —W—X—Y—Z is attached to the ε-amino group of a Lys residue present in the B chain of the parent insulin. In one more specific aspect of this embodiment, the side chain —W—X—Y—Z is attached to the ε-amino group of a Lys residue present in position 28 of the B chain. In a further more specific aspect of this embodiment, the side chain —W—X—Y—Z is attached to the ε-amino group of a Lys residue present in position 29 of the B chain. In a further more specific aspect of this embodiment, the side chain —W—X—Y—Z is attached to the ε-amino group of a Lys residue present in position 30 of the B chain.

The substructure W of the side chain —W—X—Y—Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, α-Asp, α-Glu, and γ-Glu. Further options for W are for example α-hGlu and δ-hGlu.

In a further embodiment, W is a chain composed of two α-amino add residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; α-hGlu-α-hGlu; δ-hGlu-β-Asp; δ-hGlu-γ-Glu; and δ-hGlu-δ-hGlu.

In a further embodiment, W is a chain composed of three α-amino acid residues, independently having from 4 to 10 carbon atoms, the amino acid residues of the chain being selected from the group of residues having a neutral side chain and residues having a carboxylic add group in the side chain so that the chain has at least one residue which has a carboxylic acid group in the side chain. In one embodiment, the amino acid residues are codable residues.

In a further embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In one embodiment W can be connected to the ε-amino group of the Lys residue in the B-chain via an urea derivative.

The substructure X of the side chain —W—X—Y—Z can be a group of the formula —$\underline{C}$O— that, via a bond from the underscored carbonyl carbon, forms amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —COCH(COOH)$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$$\underline{C}$OOH)CH$_2$CH$_2$CO— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

The substructure Y of the side chain —W—X—Y—Z can be a group of the formula —(CH$_2$)$_m$— where m is an integer in the range of from 6 to 32, from 8 to 20, from 12 to 20, or from 12-16.

In another embodiment, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In another embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In one embodiment, the substructure Z of the side chain —W—X—Y—Z is —COOH provided that when W is a covalent bond and X is —CO—, then Z is different from —COOH. In one embodiment Z is —COOH. In another embodiment, Z is —CO-Asp. In another embodiment, Z is —CO-Glu. In another embodiment, Z is —CO-Gly. In another embodiment, Z is —CO-Sar. In another embodiment, Z is —CH(COOH)$_2$. In another embodiment, Z is —N(CH$_2$COOH)$_2$. In another embodiment, Z is —SO$_3$H. In another embodiment, Z is —PO$_3$H.

In a further embodiment W is selected from the group consisting of α-Asp, β-Asp, α-Glu, and γ-Glu; X is —CO— or —COCH(COOH)CO; Y is —(CH$_2$)$_m$— where m is an integer in the range of 12-18 and Z is —COOH or —CH(COOH)$_2$.

The Insulin moiety—in the present text also referred to as the parent insulin—of a '347 derivative can be a naturally occurring insulin such as human insulin or porcine insulin. Alternatively, the parent insulin can be an insulin analogue.

In one group of parent insulin analogues, the amino acid residue at position A21 is Asn. In another group of parent insulin analogues, the amino acid residue at position A21 is Gly. Specific examples from this group of analogues are Gly$^{A21}$ human insulin, Gly$^{A21}$ des(B30)human insulin; and Gly$^{A21}$Arg$^{B31}$Arg$^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is Asp$^{B28}$ human insulin.

In another group of parent insulin analogues, the amino acid residue at position B28 is Lys and the amino acid residue at position B29 is Pro. A specific example from this group of parent insulin analogues is Lys$^{B28}$Pro$^{B29}$ human insulin.

In another group of parent insulin analogues the amino acid residue in position B30 is Lys and the amino acid residue in position B29 is any codable amino add except Cys, Met, Arg and Lys. An example is an insulin analogue where the amino acid residue at position B29 is Thr and the amino acid residue at position B30 is Lys. A specific example from this group of parent insulin analogues is Thr$^{B29}$Lys$^{B30}$ human insulin.

In another group of parent insulin analogues, the amino acid residue at position B3 is Lys and the amino acid residue at position B29 is Glu. A specific example from this group of parent insulin analogues is Lys$^{B3}$Glu$^{B29}$ human insulin.

In one embodiment the parent insulin is selected from the group consisting of human insulin; des(B1) human insulin; des(B30) human insulin; GlyA21 human insulin; GlyA21 des(B30)human insulin; AspB28 human insulin; porcine insulin; LysB28ProB29 human insulin; GlyA21ArgB31ArgB32 human insulin; and LysB3GluB29 human insulin.

Examples of '347 derivatives useful in the invention are the following compounds:

N$^{εB29}$—(N$^α$—(HOOC(CH$_2$)$_{14}$CO)-γ-Glu) des(B30) human insulin;

N$^{εB29}$—(N$^α$—(HOOC(CH$_2$)$_{15}$CO)-γ-Glu) des(B30) human insulin;

N$^{εB29}$—(N$^α$—(HOOC(CH$_2$)$_{16}$CO)-γ-Glu) des(B30) human insulin;

N$^{εB29}$—(N$^α$—(HOOC(CH$_2$)$_{17}$CO)-γ-Glu) des(B30) human insulin;

N$^{εB29}$—(N$^α$—(HOOC(CH$_2$)$_{18}$CO)-γ-Glu) des(B30) human insulin;

N$^{εB29}$—(N$^α$—(HOOC(CH$_2$)$_{16}$CO)-γ-Glu-N-(γ-Glu)) des(B30) human insulin;

N$^{εB29}$—(N$^α$—(Asp-OC(CH$_2$)$_{16}$CO)-γ-Glu) des(B30) human insulin;

N$^{εB29}$—(N$^α$—(Glu-OC(CH$_2$)$_{14}$CO)-γ-Glu) des(B30) human insulin;

N$^{εB29}$—(N$^α$—(Glu-OC(CH$_2$)$_{14}$CO—) des(B30) human insulin;

N$^{εB29}$—(N$^α$—(Asp-OC(CH$_2$)$_{16}$CO—) des(B30) human insulin;

N$^{εB29}$—(N$^α$—(HOOC(CH$_2$)$_{16}$CO)-α-Glu-N-(β-Asp)) des(B30) human insulin;

N$^{εB29}$—(N$^α$—(Gly-OC(CH$_2$)$_{13}$CO)-γ-Glu) des(B30) human insulin;

N$^{εB29}$—(N$^α$—(Sar-OC(CH$_2$)$_{13}$CO)-γ-Glu) des(B30) human insulin;

N$^{εB29}$—(N$^α$—(HOOC(CH$_2$)$_{13}$CO)-γ-Glu) des(B30) human insulin;

(N$^{εB29}$—(N$^α$—(HOOC(CH$_2$)$_{13}$CO)-β-Asp) des(B30) human insulin;

N$^{εB29}$—(N$^α$—(HOOC(CH$_2$)$_{13}$CO)-α-Glu) des(B30) human insulin;

N$^{εB29}$—(N$^α$—(HOOC(CH$_2$)$_{16}$CO)-γ-D-Glu) des(B30) human insulin;

N$^{εB29}$—(N$^α$—(HOOC(CH$_2$)$_{14}$CO)-β-D-Asp) des(B30) human insulin;

N$^{εB29}$—(N—HOOC(CH$_2$)$_{16}$CO-β-D-Asp) des(B30) human insulin;

N$^{εB29}$—(N—HOOC(CH$_2$)$_{14}$CO-IDA) des(B30) human insulin;

N$^{εB29}$—[N—(HOOC(CH$_2$)$_{16}$CO)—N-(carboxyethyl)-Gly] des(B30) human insulin;

N$^{εB29}$—[N—(HOOC(CH$_2$)$_{14}$CO)—N-(carboxyethyl)-Gly] des(B30) human insulin; and N$^{εB29}$—[N—(HOOC(CH$_2$)$_{14}$CO)—N-(carboxymethyl)-β-Ala] des(B30) human insulin.

In one embodiment the insulin derivative is N$^{εB29}$—(N$^α$—(HOOC(CH$_2$)$_{14}$CO)-γ-Glu) des(B30) human insulin. In one embodiment the insulin derivative is N$^{εB29}$—(N$^α$—(HOOC(CH$_2$)$_{15}$CO)-γ-Glu) des(B30) human insulin. In one embodiment the insulin derivative is N$^{εB29}$—(N$^α$—(HOOC(CH$_2$)$_{16}$CO)-γ-Glu) des(B30) human insulin. In one embodiment the insulin derivative is N$^{εB29}$—(N$^α$—(HOOC(CH$_2$)$_{17}$CO)-γ-Glu) des(B30) human insulin. In one embodiment the insulin derivative is N$^{εB29}$—(N$^α$—(HOOC(CH$_2$)$_{18}$CO)-γ-Glu) des(B30) human insulin. In one embodiment the insulin derivative is N$^{εB29}$—(N$^α$—(HOOC(CH$_2$)$_{16}$CO)-γ-Glu-N-(γ-Glu)) des(B30) human insulin. In one embodiment the insulin derivative is N$^{εB29}$—(N$^α$-(Asp-OC(CH$_2$)$_{16}$CO)-γ-Glu) des(B30) human insulin. In one embodiment the insulin derivative is N$^{εB29}$—(N$^α$-(Glu-OC(CH$_2$)$_{14}$CO)-γ-Glu) des(B30) human insulin. In one embodiment the insulin derivative is N$^{εB29}$—(N$^α$-(Glu-OC(CH$_2$)$_{14}$CO—) des(B30) human insulin. In one embodiment the insulin derivative is N$^{εB29}$—(N$^α$-(Asp-OC(CH$_2$)$_{16}$CO—) des(B30) human insulin. In one embodiment the insulin derivative is N$^{εB29}$—(N$^α$—(HOOC(CH$_2$)$_{16}$CO)-α-Glu-N-(β-Asp)) des(B30) human insulin. In one embodiment the insulin derivative is N$^{εB29}$—(N$^α$-(Gly-OC(CH$_2$)$_{13}$ CO)-γ-Glu) des(B30) human insulin. In one embodiment the insulin derivative is $N^{\varepsilon B29}$—($N^{\alpha}$-(Sar-OC(CH$_2$)$_{13}$CO)-γ-Glu) des(B30) human insulin. In one embodiment the insulin derivative is $N^{\varepsilon B29}$—($N^{\alpha}$—(HOOC(CH$_2$)$_{13}$CO)-γ-Glu) des(B30) human insulin. In one embodiment the insulin derivative is ($N^{\varepsilon B29}$—($N^{\alpha}$—(HOOC(CH$_2$)$_{13}$CO)-β-Asp) des(B30) human insulin. In one embodiment the insulin derivative is $N^{\varepsilon B29}$—($N^{\alpha}$—(HOOC(CH$_2$)$_{13}$CO)-α-Glu) des(B30) human insulin. In one embodiment the insulin derivative is $N^{\varepsilon B29}$—($N^{\alpha}$—(HOOC(CH$_2$)$_{16}$CO)-γ-D-Glu) des(B30) human insulin. In one embodiment the insulin derivative is $N^{\varepsilon B29}$—($N^{\alpha}$—(HOOC(CH$_2$)$_{14}$CO)-β-D-Asp) des(B30) human insulin. In one embodiment the insulin derivative is $N^{\varepsilon B29}$—($N^{\alpha}$—(HOOC(CH$_2$)$_{14}$CO)-β-D-Asp) des(B30) human insulin. In one embodiment the insulin derivative is $N^{\varepsilon B29}$—(N—HOOC(CH$_2$)$_{16}$CO-β-D-Asp) des(B30) human insulin. In one embodiment the insulin derivative is $N^{\varepsilon B29}$—(N—HOOC(CH$_2$)$_{14}$CO-IDA) des(B30) human insulin. In one embodiment the insulin derivative is $N^{\varepsilon B29}$—[N—(HOOC(CH$_2$)$_{16}$CO)—N-(carboxyethyl)-Gly] des(B30) human insulin. In one embodiment the insulin derivative is $N^{\varepsilon B29}$—[N—(HOOC(CH$_2$)$_{14}$CO)—N-(carboxyethyl)-Gly] des(B30) human insulin. In one embodiment the insulin derivative is $N^{\varepsilon B29}$—[N—(HOOC(CH$_2$)$_{14}$CO)—N(carboxymethyl)-β-Ala] des(B30) human insulin.

'347 derivatives may be provided in the form of essentially zinc free compounds or in the form of zinc complexes. When zinc complexes of a '347 derivative are provided, two $Zn^{2+}$ ions, three $Zn^{2+}$ ions or four $Zn^{2+}$ ions can be bound to each insulin hexamer. In one embodiment the insulin derivative is in the form of a zinc complex, wherein each insulin hexamer binds two zinc ions, three zinc ions, four zinc ions, five zinc ions, six zinc ions, seven zinc ions, eight zinc ions, nine zinc ions or ten zinc ions. Solutions of zinc complexes of the insulin derivatives will contain mixtures of such species.

Details pertaining to the preparation, formulation, pharmacology and other characteristics of relevance for the '347 derivatives are set forth in WO 2005/012347, which is hereby incorporated by reference herein.

In one embodiment substantially no other naturally occurring insulin, insulin analogue or derivative of naturally occurring insulin or insulin analogue exhibiting a prolonged profile of action is administered to said patient.

Rapid Acting Insulin Analogues

Embodiments of the method of the invention include those wherein administration of the naturally occurring insulin, insulin analogue or derivative exhibiting a prolonged profile of action is supplemented with more frequent administrations of a fast-acting naturally occurring insulin, insulin analogue or derivative and/or administration of a non-insulin antidiabetic drug.

So, one embodiment the invention provides a combination treatment, where any suitable insulin, analogue or derivative described above (e.g. $N^{\varepsilon B29}$—($N^{\alpha}$—(HOOC(CH$_2$)$_{14}$CO)-γ-L-Glu) des(B30) human insulin=$N^{\varepsilon B29}$—($N^{\alpha}$—(HOOC(CH$_2$)$_{14}$CO)-γ-Glu) des(B30) human insulin=LysB29(Nε-hexadecandioyl-γ-Glu) des(B30) human insulin=Insulin degludec (Example 4 in WO 2005/012347)) and a rapid acting insulin analogue are used in combination, e.g. in a combined product, but also administered separately. Hence, all specific disclosures in the present application which provide details relating to insulins useful in the presently disclosed invention relate mutatis mutandis to combination therapy involving the same compounds together with rapid acting insulin analogues. Typically, the rapid acting insulin is selected from the group consisting of $Asp^{B29}$ human insulin; $Lys^{B29}Pro^{B29}$ human insulin and $Lys^{B3}Glu^{B29}$ human insulin. The combined product shows no blunting. The insulin derivative disclosed in WO2005/012347 can be formulated with rapid acting insulin analogues as described in WO2007/074133, which is hereby incorporated by reference.

In one embodiment the invention provides a combination treatment with $N^{\varepsilon B29}$—($N^{\alpha}$—(HOOC(CH$_2$)$_{14}$CO)-γ-L-Glu) des(B30) human insulin and AspB28 human insulin together with pharmaceutically acceptable carriers and additives.

The Insulin derivative according to the invention and the rapid acting insulin analogue can if necessary be mixed in a ratio from about 90/10%; about 80/20%, about 70/30%, about 60/40%, about 50/50%, about 40/60%, about 30/60%, about 20/80% or about 10/90%.

Other Combinations

In one embodiment administration of the naturally occurring insulin, insulin analogue or derivative exhibiting a prolonged profile of action is supplemented with administration of a non-insulin anti-diabetic drug, such as metformin, sufonylurea and/or thiazoledinedione or such as a GLP-1 agonist.

Formulation of insulin, Insulin Analogues or Derivatives Thereof

In one embodiment the naturally occurring insulin, insulin analogue or derivative is formulated together with a pharmaceutically acceptable carrier and/or vehicle and/or diluent and/or excipient.

A pharmaceutical composition containing a naturally occurring insulin, an insulin analogue, or a derivative of a naturally occurring insulin or insulin analogue is termed "an insulin composition" herein. In order to exercise the present invention an insulin composition may be administered parenterally to patients in need of such a treatment. Parenteral administration may be performed by injection, such as subcutaneous, intramuscular or intravenous injection, by means of a syringe, optionally a pen-like syringe. In one embodiment the administration is by s.c. injection. In one embodiment the administration is by i.m. injection. In one embodiment the administration is by I.v. injection. Alternatively, parenteral administration can be performed by means of an infusion pump. Further options are to administer the insulin composition nasally or pulmonally, preferably in compositions, powders or liquids, specifically designed for the purpose.

Injectable insulin compositions can be prepared using the conventional techniques of the pharmaceutical industry which involve dissolving and mixing the ingredients as appropriate to give the desired end product. Thus, according to one procedure, a natural insulin, analogue or derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer is typically selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative useful in embodiments of the invention.

In a further embodiment of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy,* 19th edition, 1995.

In a further embodiment of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy,* 19th edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid), TRIS (2-amino-2-hydroxymethyl-1,3-propandiol), and sodium phosphate.

A composition for nasal administration may, for example, be prepared as described in European Patent No. 272097 (to Novo Nordisk A/S).

Insulin compositions containing can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin, analogue or derivative employed, the age, body weight, physical activity, and diet of the patient, on a possible combination with other drugs, and on the severity of the state to be treated. It is recommended that the dosage regimen be determined for each individual patient by those skilled in the art in a similar way as for known insulin compositions, however taking into consideration the present teachings concerning dosage intervals.

Where expedient, the insulin compositions may be used in combination with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

In one embodiment the composition of the invention is as defined in WO 2007/074133 or WO2008/152106.

Use as a Medicament

In one embodiment the present invention is used in the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation. In one embodiment the diabetes mellitus is type 1 or 2 diabetes. In one embodiment the diabetes mellitus is type 2 diabetes, which fails oral anti-diabetic treatment.

In one embodiment the present invention relates to a naturally occurring insulin, an insulin analogue, or a derivative of a naturally occurring insulin or insulin analogue for use in a method as defined herein. In one embodiment the present invention relates to the use of a naturally occurring insulin, an insulin analogue, or a derivative of a naturally occurring insulin or insulin analogue in the preparation of a pharmaceutical composition for treatment of diabetes mellitus or other conditions characterized by hyperglycaemia, prediabetes, impaired glucose tolerance, metabolic syndrome, obesity, cachexia, in vivo beta-cell loss/death, excessive appetite, and inflammation, wherein the treatment is as defined herein.

In one embodiment the invention relates to instructions for use comprising a description of a method as defined herein.

Embodiments Of The Invention

The Invention will further be summarized in the following embodiments:

1. A method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein at least one of said intervals has a length of
  a) at least 1.04 times the mean of said intervals, or
  b) no more than 0.96 times the mean of said intervals.

2. A method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein the mean of said intervals is less than 56 hours and at least one of said intervals is
a) at least 1.04 times the mean of said intervals, or
b) no more than 0.96 times the mean of said intervals.

3. A method for treatment of a condition or disease where administration of insulin will be of benefit, comprising administering, to a patient in need thereof, effective dosages of a naturally occurring insulin, an insulin analogue or a derivative of a naturally occurring insulin or of an insulin analogue, wherein said insulin exhibits a prolonged profile of action and wherein said dosages are administered at intervals, wherein at least one of said intervals has a length of
a) at least 1.3 times the mean of said intervals, or
b) no more than 0.85 times the mean of said intervals.

4. The method according to any one of the preceding embodiments, wherein said intervals are not selected from the group consisting of
a) administration at 3 fixed weekdays, such as Monday-Wednesday-Friday; Monday-Wednesday-Saturday; Monday-Thursday-Saturday; Tuesday-Thursday-Saturday; Tuesday-Thursday-Sunday; and Tuesday-Friday-Sunday; or
b) administration at 2 fixed weekdays, such as Monday-Thursday; Monday-Friday; Tuesday-Friday; Tuesday-Saturday; Wednesday-Saturday; Wednesday-Sunday; and Thursday-Sunday.

5. The method according to any one of the preceding embodiments, wherein at least two, such as at least three or at least four, of said intervals have a length of a) at least 1.04 times the mean of said intervals, or b) no more than 0.96 times the mean of said intervals.

6. The method according to any one of the preceding embodiments, wherein at least five, such as at least ten or at least twenty, of said intervals have a length as defined in embodiment 5.

7. The method according to any one of the preceding embodiments, wherein at least 1/1000, such as at least 1/500 or at least 1/300, of said intervals have a length as defined in embodiment 5.

8. The method according to any one of the preceding embodiments, wherein at least 1/200, such as at least 1/100 or at least 1/50, of said intervals have a length as defined in embodiment 5.

9. The method according to any one of the preceding embodiments, wherein at least 1/40, such as at least 1/30 or at least 1/20, of said intervals have a length as defined in embodiment 5.

10. The method according to any one of the preceding embodiments, wherein at least 1/15, such as at least 1/10 or at least 1/5, of said intervals have a length as defined in embodiment 5.

11. The method according to any one of the preceding embodiments, wherein at least 1/3, such as at least 1/2 or all, of said intervals have a length as defined in embodiment 5.

12. The method according to any one of the preceding embodiments, wherein said dosage is not adjusted between administrations.

13. The method according to any one of the preceding embodiments, wherein said dosage is substantially the same at every administration.

14. The method according to any one of the preceding embodiments, wherein said intervals occur over a period of at least 3 weeks, such as at least 10 weeks or at least 26 weeks.

Dosage Intervals

15. The method according to any one of the preceding embodiments, wherein at least one of said intervals is at least the mean of said intervals plus 1/24 times the mean of said intervals, such as at least the mean of said intervals plus 1.5/24 times the mean of said intervals.

16. The method according to any one of the preceding embodiments, wherein at least one of said intervals is at least the mean of said intervals plus 2/24 times the mean of said intervals, such as at least the mean of said intervals plus 2.5/24 times the mean of said intervals.

17. The method according to any one of the preceding embodiments, wherein at least one of said intervals is at least the mean of said intervals plus 3/24 times the mean of said intervals.

18. The method according to any one of the preceding embodiments, wherein at least one of said intervals is at least the mean of said intervals plus 3.5/24 times the mean of said intervals.

19. The method according to any one of the preceding embodiments, wherein at least one of said intervals is at least the mean of said intervals plus 4/24 times the mean of said intervals.

20. The method according to any one of the preceding embodiments, wherein at least one of said intervals is at least the mean of said intervals plus 5/24 times the mean of said intervals.

21. The method according to any one of the preceding embodiments, wherein at least one of said intervals is no more than the mean of said intervals minus 1/24 times the mean of said intervals, such as no more than the mean of said intervals minus 1.5/24 times the mean of said intervals.

22. The method according to any one of the preceding embodiments, wherein at least one of said intervals is no more than the mean of said intervals minus 2/24 times the mean of said intervals, such as no more than the mean of said intervals minus 2.5/24 times the mean of said intervals.

23. The method according to any one of the preceding embodiments, wherein at least one of said intervals is no more than the mean of said intervals minus 3/24 times the mean of said intervals.

24. The method according to any one of the preceding embodiments, wherein at least one of said intervals is no more than the mean of said intervals minus 3.5/24 times the mean of said intervals.

25. The method according to any one of the preceding embodiments, wherein at least one of said intervals is no more than the mean of said intervals minus 4/24 times the mean of said intervals.

26. The method according to any one of the preceding embodiments, wherein at least one of said intervals is no more than the mean of said intervals minus 5/24 times the mean of said intervals.

27. The method according to any one of the preceding embodiments, wherein at least one of said intervals is at least 1.1 times, such as at least 1.15 times, the mean of said intervals.

28. The method according to any one of the preceding embodiments, wherein at least one of said intervals is at least 1.2 times, such as at least 1.25 times, the mean of said intervals.

29. The method according to any one of the preceding embodiments, wherein at least one of said intervals is at least 1.3 times, such as at least 1.35 times, the mean of said intervals.

30. The method according to any one of the preceding embodiments, wherein at least one of said intervals is at least 1.4 times the mean of said intervals.

31. The method according to any one of the preceding embodiments, wherein at least one of said intervals is at least 1.45 times the mean of said intervals.

32. The method according to any one of the preceding embodiments, wherein at least one of said intervals is at least 1.5 times the mean of said intervals.

33. The method according to any one of the preceding embodiments, wherein at least one of said intervals is at least 1.55 times the mean of said intervals.

34. The method according to any one of the preceding embodiments, wherein at least one of said intervals is at least 1.6 times the mean of said intervals.

35. The method according to any one of the preceding embodiments, wherein at least one of said intervals is at least 1.65 times the mean of said intervals.

36. The method according to any one of the preceding embodiments, wherein at least one of said intervals is at least 1.7 times the mean of said intervals.

37. The method according to any one of the preceding embodiments, wherein at least one of said intervals is at least 1.75 times the mean of said intervals.

38. The method according to any one of the preceding embodiments, wherein at least one of said intervals is no more than 0.95 times the mean of said intervals.

39. The method according to any one of the preceding embodiments, wherein at least one of said intervals is no more than 0.90 times the mean of said intervals.

40. The method according to any one of the preceding embodiments, wherein at least one of said intervals is no more than 0.85 times the mean of said intervals.

41. The method according to any one of the preceding embodiments, wherein at least one of said intervals is no more than 0.80 times the mean of said intervals.

42. The method according to any one of the preceding embodiments, wherein at least one of said intervals is no more than 0.75 times the mean of said intervals.

43. The method according to any one of the preceding embodiments, wherein at least one of said intervals is no more than 0.70 times the mean of said intervals.

44. The method according to any one of the preceding embodiments, wherein at least one of said intervals is no more than 0.65 times the mean of said intervals.

45. The method according to any one of the preceding embodiments, wherein at least one of said intervals is no more than 0.60 times the mean of said intervals.

46. The method according to any one of the preceding embodiments, wherein at least one of said intervals is no more than 0.55 times the mean of said intervals.

47. The method according to any one of the preceding embodiments, wherein at least one of said intervals is no more than 0.50 times the mean of said intervals.

48. The method according to any one of the preceding embodiments, wherein at least one of said intervals is no more than 0.45 times the mean of said intervals.

49. The method according to any one of the preceding embodiments, wherein at least one of said intervals is no more than 0.40 times the mean of said intervals.

50. The method according to any one of the preceding embodiments, wherein at least one of said intervals is no more than 0.35 times the mean of said intervals.

51. The method according to any one of the preceding embodiments, wherein at least one of said intervals is no more than 0.30 times the mean of said intervals.

52. The method according to any one of the preceding embodiments, wherein the mean of said intervals is less than 48 hours, such as less than 42 hours or less than 36 hours.

53. The method according to any one of the preceding embodiments, wherein the mean of said intervals is less than 30 hours, such as less than 24 hours or less than 18 hours.

54. The method according to any one of the preceding embodiments, wherein the mean of said intervals is at least 8 hours, such at least 12 hours or at least 16 hours.

55. The method according to any one of the preceding embodiments, wherein the mean of said intervals is at least 20 hours, such as at least 24 hours or at least 28 hours.

56. The method according to any one of the preceding embodiments, wherein the mean of said intervals is at least 12 hours, such as at least 24 hours or at least 36 hours.

57. The method according to any one of the preceding embodiments, wherein the mean of said intervals is at least 48 hours, such as at least 72 hours or at least 96 hours.

58. The method according to any one of the preceding embodiments, wherein the mean of said intervals is at least 120 hours, such as at least 144 hours or at least 168 hours.

59. The method according to any one of the preceding embodiments, wherein the mean of said intervals is at least 182 hours, such as at least 206 hours or at least 230 hours.

60. The method according to any one of the preceding embodiments, wherein said dosages are administered every day or every second day.

61. The method according to any one of the preceding embodiments, wherein at least one of said intervals is between 8 and 22 hours, such as between 8 and 20 hours or between 8 and 18 hours.

62. The method according to any one of the preceding embodiments, wherein at least one of said intervals is between 8 and 16 hours, such as between 8 and 14 hours or between 8 and 12 hours.

63. The method according to any one of the preceding embodiments, wherein at least one of said intervals is between 26 and 40 hours, such as between 28 and 40 hours or between 30 and 40 hours.

64. The method according to any one of the preceding embodiments, wherein at least one of said intervals is between 32 and 40 hours, such as between 34 and 40 hours or between 36 and 40 hours.

65. The method according to any one of the preceding embodiments, wherein at least one of said intervals is between 4 and 11 hours, such as between 4 and 10 hours or between 4 and 9 hours.

66. The method according to any one of the preceding embodiments, wherein at least one of said intervals is between 4 and 8 hours, such as between 4 and 7 hours or between 4 and 6 hours.

67. The method according to any one of the preceding embodiments, wherein at least one of said intervals is between 13 and 20 hours, such as between 14 and 20 hours or between 15 and 20 hours.

68. The method according to any one of the preceding embodiments, wherein at least one of said intervals is between 16 and 20 hours, such as between 17 and 20 hours or between 18 and 20 hours.
69. The method according to any one of the preceding embodiments, wherein at least one of said intervals is between 16 and 22 hours, such as between 16 and 20 hours or between 16 and 18 hours.
70. The method according to any one of the preceding embodiments, wherein at least one of said intervals is between 16 and 16 hours, such as between 16 and 14 hours or between 16 and 12 hours.
71. The method according to any one of the preceding embodiments, wherein at least one of said intervals is between 52 and 80 hours, such as between 56 and 80 hours or between 60 and 80 hours.
72. The method according to any one of the preceding embodiments, wherein at least one of said intervals is between 64 and 80 hours, such as between 68 and 80 hours or between 72 and 80 hours.

Insulin Derivative

73. The method according to any one of the preceding embodiments, wherein administration of the naturally occurring insulin, insulin analogue or derivative exhibiting a prolonged profile of action is supplemented with more frequent administrations of a fast-acting naturally occurring insulin, insulin analogue or derivative and/or administration of a non-insulin anti-diabetic drug.
74. The method according to any one of the preceding embodiments, wherein substantially no other naturally occurring insulin, insulin analogue or derivative of naturally occurring insulin or insulin analogue exhibiting a prolonged profile of action is administered to said patient.
75. The method according to any one of the preceding embodiments, wherein administration of the naturally occurring insulin, insulin analogue or derivative exhibiting a prolonged profile of action is supplemented administration of a non-insulin anti-diabetic drug.
76. The method according to any one of the preceding embodiments, wherein the insulin for use in the present invention is an insulin analogue or a derivative thereof.
77. The method according to any one of the preceding embodiments, wherein a derivative of said naturally occurring insulin or said insulin analogue is administered and wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
- an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
- a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
- a covalent bond from X to the α-amino group of the N-terminal amino acid residue of the B chain or to the ε-amino group of a Lys residue present in the B chain of the parent insulin;

X is:
- —CO—;
- —COCH(COOH)C̲O—;
- —CON(CH$_2$COOH)CH$_2$C̲O—;
- —CON(CH$_2$COOH)CH$_2$CON(CH$_2$COOH)CH$_2$C̲O—;
- —CON(CH$_2$CH$_2$COOH)CH$_2$CH$_2$C̲O—;
- a —CON(CH$_2$CH$_2$COOH)CH$_2$CH$_2$CON(CH$_2$CH$_2$COOH)CH$_2$CH$_2$C̲O—;
- —CONHCH(COOH)(CH$_2$)$_4$NHC̲O—;
- —CON(CH$_2$CH$_2$COOH)CH$_2$C̲O—; or
- —CON(CH$_2$COOH)CH$_2$CH$_2$C̲O— that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
- —(CH$_2$)$_m$— where m is an integer in the range of 6 to 32;
- a divalent hydrocarbon chain comprising 1, 2 or 3 —CH=CH— groups and a number of —CH$_2$— groups sufficient to give a total number of carbon atoms in the chain in the range of 10 to 32;
- a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
- —COOH;
- —CO-Asp;
- —CO-Glu;
- —CO-Gly;
- —CO-Sar;
- —CH(COOH)$_2$;
- —N(CH$_2$COOH)$_2$;
- —SO$_3$H; or
- —PO$_3$H;

and any Zn$^{2+}$ complexes thereof, provided that when W is a covalent bond and X is —CO—, then Z is different from —COOH.

78. The method according to embodiment 77, wherein side chain —W—X—Y—Z is attached to the α-amino group of the N-terminal amino acid residue of the B chain of the parent insulin.
79. The method according to embodiment 77, wherein side chain —W—X—Y—Z is attached to the ε-amino group of a Lys residue present in the B chain of the parent insulin.
80. The method according to any one of embodiments 77-79, wherein W is a covalent bond.
81. The method according to any one of embodiments 77-79, wherein W is an α-amino acid residue having from 4 to 10 carbon atoms.
82. The method according to embodiment 81, wherein W is selected from the group consisting of α-Asp, β-Asp, α-Glu, γ-Glu, α-hGlu and δ-hGlu.
83. The method according to any one of embodiments 77-79, wherein W is a chain composed of two α-amino acid residues of which one has from 4 to 10 carbon atoms and a free carboxylic acid group while the other has from 2 to 11 carbon atoms but no free carboxylic acid group.

84. The method according to embodiment 83, wherein W is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

85. The method according to any one of embodiments 77-79, wherein W is a chain composed of two α-amino acid residues, independently having from 4 to 10 carbon atoms, and both having a free carboxylic acid group.

86. The method according to embodiment 85, wherein W is selected from the group consisting of α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

87. The method according to any one of embodiments 77-86, wherein X is —CO— or —COCH(COOH)CO—.

88. The method according to any one of embodiments 77-87, wherein X is
—CON(CH$_2$COOH)CH$_2$C̲O—;
—CON(CH$_2$COOH)CH$_2$CON(CH$_2$COOH)CH$_2$C̲O—;
—CON(CH$_2$CH$_2$COOH)CH$_2$CH$_2$C̲O—;
—CON(CH$_2$CH$_2$COOH)CH$_2$CH$_2$CON(CH$_2$CH$_2$COOH)CH$_2$CH$_2$C̲O—
—CON(CH$_2$CH$_2$COOH)CH$_2$C̲O—; or
—CON(CH$_2$COOH)CH$_2$CH$_2$C̲O—.

89. The method according to any one of embodiments 77-88, wherein Y is —(CH$_2$)$_m$— where m is an integer in the range of from 6 to 32, from 8 to 20, from 12 to 20 or from 12-16.

90. The method according to any one of embodiments 77-89, wherein Z is —COOH.

91. The method according to any one of embodiments 77-89, wherein Z is —CH(COOH)$_2$.

92. The method according to any one of embodiments 77-89, wherein Z is —N(CH$_2$COOH)$_2$.

93. The method according to any one of embodiments 77-89, wherein Z is —SO$_3$H.

94. The method according to any one of embodiments 77-89, wherein Z is —PO$_3$H.

95. The method according to any one of embodiments 77-94, wherein the parent insulin has Asn or Gly at position A21.

96. The method according to any one of embodiments 77-94, wherein the parent insulin is a des(B1) analogue.

97. The method according to any one of embodiments 77-94, wherein the parent insulin is a des(B30) analogue.

98. The method according to any one of embodiments 77-94, wherein position B29 in the parent insulin can be any codable amino acid except Cys, Met, Arg and Lys and the amino acid in position B30 is Lys.

99. The method according to any one of embodiments 77-94, wherein the parent insulin has Thr at position B29 and Lys at position B30.

100. The method according to any one of embodiments 77-94, wherein the parent insulin is selected from the group consisting of human insulin; des(B1) human insulin; des(B30) human insulin; Gly$^{A21}$ human insulin; Gly$^{A21}$ des(B30)human insulin; Asp$^{B29}$ human insulin; porcine insulin; Lys$^{B28}$Pro$^{B29}$ human insulin; Gly$^{A21}$Arg$^{B31}$Arg$^{B32}$ human insulin; and Lys$^{B3}$Glu$^{B9}$ human insulin.

101. The method according to embodiment 77, wherein the insulin derivative is selected from the group consisting of N$^{εB29}$—(N$^α$—(HOOC(CH$_2$)$_{14}$CO)-γ-Glu) des(B30) human insulin; N$^{εB29}$—(N$^α$—(HOOC(CH$_2$)$_{15}$CO)-γ-Glu) des(B30) human insulin; N$^{εB29}$—(N$^α$—(HOOC(CH$_2$)$_{16}$CO)-γ-Glu) des(B30) human insulin; N$^{εB29}$—(N$^α$—(HOOC(CH$_2$)$_{17}$CO)-γ-Glu) des(B30) human insulin; N$^{εB29}$—(N$^α$—(HOOC(CH$_2$)$_{17}$CO)-γ-Glu) des(B30) human insulin; N$^{εB29}$—(N$^α$—(HOOC(CH$_2$)$_{16}$CO)-γ-Glu-N-(γ-Glu)) des(B30) human insulin; N$^{εB29}$—(N$^α$-(Asp-OC(CH$_2$)$_{16}$CO)-γ-Glu) des(B30) human insulin; N$^{εB29}$—(N$^α$-(Glu-OC(CH$_2$)$_{14}$CO)-γ-Glu) des(B30) human insulin; N$^{εB29}$—(N$^α$-(Glu-OC(CH$_2$)$_{14}$CO—) des(B30) human insulin; N$^{εB29}$—(N$^α$-(Asp-OC(CH$_2$)$_{16}$CO—) des(B30) human insulin; N$^{εB29}$—(N$^α$—(HOOC(CH$_2$)$_{16}$CO)-α-Glu-N-(β-Asp)) des(B30) human insulin; N$^{εB29}$—(N$^α$-(Gly-OC(CH$_2$)$_{13}$CO)-γ-Glu) des(B30) human insulin; N$^{εB29}$—(N$^α$-(Sar-OC(CH$_2$)$_{13}$CO)-γ-Glu) des(B30) human insulin; N$^{εB29}$—(N$^α$—(HOOC(CH$_2$)$_{13}$CO)-γ-Glu) des(B30) human insulin; (N$^{εB29}$—(N$^α$—(HOOC(CH$_2$)$_3$CO)—β-Asp) des(B30) human insulin; N$^{εB29}$—(N$^α$—(HOOC(CH$_2$)$_{13}$CO)-α-Glu) des(B30) human insulin; N$^{εB29}$—(N$^α$—(HOOC(CH$_2$)$_{16}$CO)-γ-D-Glu) des(B30) human insulin; N$^{εB29}$—(N—(HOOC(CH$_2$)$_{14}$CO)-β-D-Asp) des(B30) human insulin; N$^{εB29}$—(N—(HOOC(CH$_2$)$_{14}$CO)-β-D-Asp) des(B30) human insulin; N$^{εB29}$—(N—HOOC(CH$_2$)$_{16}$CO-β-D-Asp) des(B30) human insulin; N$^{εB29}$—(N—HOOC(CH$_2$)$_{14}$CO-IDA) des(B30) human insulin; N$^{εB29}$—[N—(HOOC(CH$_2$)$_{16}$CO)—N(carboxyethyl)-Gly] des(B30) human insulin; N$^{εB29}$—[N—(HOOC(CH$_2$)$_{14}$CO)—N(carboxyethyl)-Gly] des(B30) human insulin; and N$^{εB29}$—[N—(HOOC(CH$_2$)$_{14}$CO)—N(carboxymethyl)-β-Ala] des(B30) human insulin.

102. The method according to embodiment 101, wherein the insulin derivative is N$^{εB29}$—(N$^α$—(HOOC(CH$_2$)$_{14}$CO)-γ-Glu) des(B30) human insulin.

103. The method according to embodiment 101, wherein the insulin derivative is N$^{εB29}$—(N$^α$—(HOOC(CH$_2$)$_{15}$CO)-γ-Glu) des(B30) human insulin.

104. The method according to embodiment 101, wherein the insulin derivative is N$^{εB29}$—(N$^α$—(HOOC(CH$_2$)$_{16}$CO)-γ-Glu) des(B30) human insulin.

105. The method according to embodiment 101, wherein the insulin derivative is N$^{εB29}$—(N$^α$—(HOOC(CH$_2$)$_{17}$CO)-γ-Glu) des(B30) human insulin.

106. The method according to embodiment 101, wherein the insulin derivative is N$^{εB29}$—(N$^α$—(HOOC(CH$_2$)$_{18}$CO)-γ-Glu) des(B30) human insulin.

107. The method according to embodiment 101, wherein the insulin derivative is N$^{εB29}$—(N$^α$—(HOOC(CH$_2$)$_{16}$C)-γ-Glu-N-(γ-Glu)) des(B30) human insulin.

108. The method according to embodiment 101, wherein the insulin derivative is N$^{εB29}$—(N$^α$-(Asp-OC(CH$_2$)$_{16}$CO)-γ-Glu) des(B30) human insulin.

109. The method according to embodiment 101, wherein the insulin derivative is N$^{εB29}$—(N$^α$-(Glu-OC(CH$_2$)$_{14}$CO)-γ-Glu) des(B30) human insulin.

110. The method according to embodiment 101, wherein the insulin derivative is N$^{εB29}$—(N$^α$-(Glu-OC(CH$_2$)$_{14}$CO—) des(B30) human insulin.

111. The method according to embodiment 101, wherein the insulin derivative is N$^{εB29}$—(N$^α$-(Asp-OC(CH$_2$)$_{16}$CO—) des(B30) human insulin.

112. The method according to embodiment 101, wherein the insulin derivative is N$^{εB29}$—(N$^α$—(HOOC(CH$_2$)$_{16}$CO)-α-Glu-N—(O-Asp)) des(B30) human insulin.

113. The method according to embodiment 101, wherein the insulin derivative is $N^{\varepsilon B29}$—($N^\alpha$-(Gly-OC(CH$_2$)$_{13}$CO)-γ-Glu) des(B30) human insulin.
114. The method according to embodiment 101, wherein the insulin derivative is $N^{\varepsilon B29}$—($N^\alpha$-(Sar-OC(CH$_2$)$_{13}$CO)-γ-Glu) des(B30) human insulin.
115. The method according to embodiment 101, wherein the insulin derivative is $N^{\varepsilon B29}$—($N^\alpha$—(HOOC(CH$_2$)$_{13}$CO)-γ-Glu) des(B30) human insulin.
116. The method according to embodiment 101, wherein the insulin derivative is ($N^{\varepsilon B29}$—($N^\alpha$—(HOOC(CH$_2$)$_{13}$CO)-β-Asp) des(B30) human insulin.
117. The method according to embodiment 101, wherein the insulin derivative is $N^{\varepsilon B29}$—($N^\alpha$—(HOOC(CH$_2$)$_{13}$CO)-α-Glu) des(B30) human insulin.
118. The method according to embodiment 101, wherein the insulin derivative is $N^{\varepsilon B29}$—($N^\alpha$—(HOOC(CH$_2$)$_{16}$CO)-γ-D-Glu) des(B30) human insulin.
119. The method according to embodiment 101, wherein the insulin derivative is $N^{\varepsilon B29}$—($N^\alpha$—(HOOC(CH$_2$)$_{14}$CO)-β-D-Asp) des(B30) human insulin.
120. The method according to embodiment 101, wherein the insulin derivative is $N^{\varepsilon B29}$—($N^\alpha$—(HOOC(CH$_2$)$_{14}$CO)-β-D-Asp) des(B30) human insulin.
121. The method according to embodiment 101, wherein the insulin derivative is $N^{\varepsilon B29}$—(N—HOOC(CH$_2$)$_{16}$CO-β-D-Asp) des(B30) human insulin.
122. The method according to embodiment 101, wherein the insulin derivative is $N^{\varepsilon B29}$—(N—HOOC(CH$_2$)$_{14}$CO-IDA) des(B30) human insulin.
123. The method according to embodiment 101, wherein the insulin derivative is $N^{\varepsilon B29}$—[N—(HOOC(CH$_2$)$_{16}$CO)—N-(carboxyethyl)-Gly] des(B30) human insulin.
124. The method according to embodiment 101, wherein the insulin derivative is $N^{\varepsilon B29}$—[N—(HOOC(CH$_2$)$_{14}$CO)—N-(carboxyethyl)-Gly] des(B30) human insulin.
125. The method according to embodiment 101, wherein the insulin derivative is $N^{\varepsilon B29}$—[N—(HOOC(CH$_2$)$_4$CO)—N-(carboxymethyl)-β-Ala] des(B30) human insulin.
126. The method according to any one of the preceding embodiments, wherein the insulin derivative is in the form of a zinc complex, wherein each insulin hexamer binds two zinc ions, three zinc ions, four zinc ions, five zinc ions, six zinc ions, seven zinc ions, eight zinc ions, nine zinc ions or ten zinc ions.

Use as a Medicament

127. The method according to any one of the preceding embodiments, wherein the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation.
128. The method according to embodiment 127, wherein the diabetes mellitus is type 1 or 2 diabetes.
129. The method according to embodiment 128, wherein the diabetes mellitus is type 2 diabetes, which fails oral anti-diabetic treatment.
130. The method according to any one of the preceding embodiments, wherein the naturally occurring insulin, analogue or derivative is administered by injection.
131. The method according to any one of the preceding embodiments, wherein the naturally occurring insulin, analogue or derivative is administered by s.c. Injection.
132. The method according to any one of the preceding embodiments, wherein the naturally occurring insulin, analogue or derivative is administered by i.m. injection.
133. The method according to any one of the preceding embodiments, wherein the naturally occurring insulin, analogue or derivative is administered by i.v. Injection.
134. The method according to any one of the preceding embodiments, wherein the naturally occurring insulin, insulin analogue or derivative is formulated together with a pharmaceutically acceptable carrier and/or vehicle and/or diluent and/or excipient.
135. A naturally occurring insulin, an insulin analogue, or a derivative of a naturally occurring insulin or insulin analogue for use in a method as defined in any one of embodiments 1-134.
136. Use of a naturally occurring insulin, an insulin analogue, or a derivative of a naturally occurring insulin or insulin analogue in the preparation of a pharmaceutical composition for treatment of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation, wherein the treatment is as defined in any one of embodiments 1-134.
137. Instructions for use comprising a description of a method as defined in any one of the claims 1-134.

The present invention is further illustrated by the following examples which, however, are not to be construed as limiting the scope of protection.

EXAMPLES

To investigate the clinical effect of an insulin product, a clinical trial has to be conducted under conditions representing the mode of use of the invention. Clinical trials investigating compounds for the treatment of diabetes with the purpose of obtaining approval and registration are subject to guidelines provided by regional authorities (the European guideline serves as an example: Note for Guidance on Clinical Investigations of Medicinal Products in the Treatment of diabetes Mellitus, EMEA, London, 2002).

As an example representing any insulin analogue with sufficiently long duration of action LysB29(Nε-hexadecandioyl-γ-Glu) des(B30) human insulin corresponding to $N^{\varepsilon B29}$—($N^\alpha$—(HOOC(CH$_2$)$_{14}$CO)-γ-L-Glu) des(B30) human insulin (Example 4 in WO 2005/012347; in the following "LysB29(Nε-hexadecandioyl-γ-Glu) des(B30) human insulin") was investigated with respect to the clinical effect with varying injection intervals.

Example 1

Steady State Clamp—Investigating Activity Profile and Duration of Action of LysB29(Nε-Hexadecandioyl-γ-Glu) des(B30) human insulin.

Methodology

The investigation was performed as a randomised, double-blind, single centre, two-period cross over trial to compare the activity profiles of LysB29(Nε-hexadecandioyl-γ-Glu) des(B30) human insulin and insulin glargine (IGlar) in subjects with type 1 diabetes.

Subjects were randomised to different sequences of subcutaneous (s.c.) multiple-dose once daily administration of LysB29(Nε-hexadecandioyl-γ-Glu) des(B30) human insulin and IGlar. The doses were either 0.57 U/kg or 0.85 U/kg of LysB29(Nε-hexadecandioyl-γ-Glu) des(B30) human insulin and 0.4 U/kg or 0.6 U/kg IGlar. The subjects were treated for 8 days for each dosing period. There was a washout period lasting 10-20 days between the two dosing periods.

At the last day of each dosing period subjects received a controlled intravenous infusion of glucose and human soluble insulin (Actrapid®) for 8-4 hours prior to trial drug administration in order to keep the blood glucose concentration stable at a level of 100 mg/dL (5.5 mmol/L), i.e. a euglycaemic clamp with a target blood glucose level of 100 mg/dL (5.5 mmol/L) was initiated. The euglycaemic clamp was terminated at 42 hours post-dosing but earlier if blood glucose levels increased to concentrations above 200 mg/dL (11.1 mmol/L) with no glucose infusion during the last 30 min.

Blood samples for measurement of serum LysB29(Nε-hexadecandioyl-γ-Glu) des(B30) human insulin/plasma IGlar, and blood glucose were drawn before dosing and for up to 146 hours after dosing.

Standard safety assessments were performed.

Number of Subjects 21 subjects completed the trial.

Diagnosis and Main Criteria for Inclusion

Male or female subjects with type 1 diabetes (≥12 months) aged 18-69 years (inclusive), with glycosylated haemoglobin (HbA$_{1c}$)≤10% and normally treated with insulin (≤1.2 U/kg/day). Subjects should have been treated with insulin ≤12 months and have a body mass index (BMI) of 18-28 kg/m$^2$ (inclusive) and a fasting C-peptide <0.3 nmol/L.

Test Product, Dose and Mode of Administration

Multiple doses of 0.57 U/kg or 0.85 U/kg of LysB29(Nε-hexadecandioyl-γ-Glu) des(B30) human insulin, 600 nmol/ml, LysB29(Nε-hexadecandioyl-γ-Glu) des(B30) human insulin, delivered in 3 ml FlexPen® (100 DU/ml) cartridge using NovoFine® 30G, 8 mm needles.

Duration of Treatment

Multiple doses of LysB29(Nε-hexadecandioyl-γ-Glu) des(B30) human insulin and IGlar were administered using during two different dosing periods lasting 8 days (optionally +1-5 days) at intervals of 10-20 days.

Reference Therapy, Dose and Mode of Administration

Multiple doses (0.4 U/lg or 0.6 U/kg) of IGlar (Lantus®), 100 IU/mL, 600 nmol/mL delivered in 3.0 mL 3 mL Optiset® cartridges and injected s.c. in the thigh using PenFine® 31G, 8 mm.

Criteria for Evaluation—Efficacy

Pharmacodynamics:

Glucose Infusion rate (GIR) during a euglycaemic clamp for 42 hours during the 8$^{th}$ and last dosing day.

Blood glucose concentrations.

Pharmacokinetics:

Serum LysB29(Nε-hexadecandioyl-γ-Glu) des(B30) human insulin/plasma IGlar concentrations for 144 hours following a single dose of either LysB29(Nε-hexadecandioyl-γ-Glu) des(B30) human insulin or IGlar.

Primary Endpoint:

AUCGIR(0-24 h), the area under the curve (AUC) of the GIR curve from 0 to 24 hours Key Secondary Endpoints:

Blood glucose level during euglycaemic clamp period
Pharmacokinetics (tmax, terminal half-life)

Demography of Trial Population

The 35 male and 7 female subjects with type 1 diabetes were aged 40 years on average, respectively, mean weight was 75 kg, mean HbA1c was 7.8%, and they had a mean diabetes duration of 21 years.

Key Results

The AUCGIR(0-24 h) for LysB29(Nε-hexadecandioyl-γ-Glu) des(B30) human insulin, did not capture the total insulin action, since pronounced levels of GIR were still present at the 24 hour time point. GIR levels at 24 hours were approximately 2.0 and 3.0 mg/kg/min for LysB29(Nε-hexadecandioyl-γ-Glu) des(B30) human insulin after the low or high dose, respectively. The corresponding values for insulin glargine were approximately 0.8 and 1.8 mg/kg/min.

Mean GIRmax was higher for IGlar (5.6 and 4.2 mg/kg/min) than for LysB29(Nε-hexadecandioyl-γ-Glu) des(B30) human insulin (4.68 and 4.02 mg/kg/min, respectively), after the highest dose but GIRmax was equal after the lower doses (3.07 mg/kg/min).

Mean GIR Time to GIRmax was longer for LysB29(Nε-hexadecandioyl-γ-Glu) des(B30) human insulin (13.2 hours and 6.1 for low and high dose respectively) than for IGlar (5.0 and 4.1 hours for low and high dose, respectively)

Mean peak to trough ranges were less for LysB29(Nε-hexadecandioyl-γ-Glu) des(B30) human insulin than after insulin glargine. The values were 1.0 and 0.7 mg/kg/min after the low and high dose, respectively. For insulin glargine the corresponding values were 1.6 and 1.1 mg/kg/min.

Average time to loss of glucose control was longer for LysB29(Nε-hexadecandioyl-γ-Glu) des(B30) human insulin than for glargine at both dose levels. This occurred after approximately 40 hours after the low LysB29(Nε-hexadecandioyl-γ-Glu) des(B30) human insulin dose and no significant loss of glucose control (defined as an increase of blood glucose of more than a 10 mg/dl) was seen at the 42 hours time point after the high LysB29(Nε-hexadecandioyl-γ-Glu) des(B30) human insulin dose. After insulin glargine dosing the loss of glucose control occurred after approximately 24 hours and 26 hours when administering the low and high dose, respectively.

The mean time to the maximum concentration (Cmax) was shorter for insulin glargine than for LysB29(Nε-hexadecandioyl-γ-Glu) des(B30) human insulin. For insulin glargine the values were 7.2 and 6.4 hours whereas the values for LysB29(Nε-hexadecandioyl-γ-Glu) des(B30) human insulin were 9.2 and 10.1 hours after the middle and high dose, respectively.

The mean terminal half-life was 25.2 hours (95% CI 23 to 28 hours) for LysB29(Nε-hexadecandioyl-γ-Glu) des(B30) human insulin and 13.9 hours (95% CI 13 to 15) hours for IGlar.

Key Safety Results

In general, multiple-dose administration of LysB29(Nε-hexadecandioyl-γ-Glu) des(B30) human insulin and IGlar, respectively, was well tolerated in subjects with type 1 diabetes.

Key Conclusions

Figure 2:
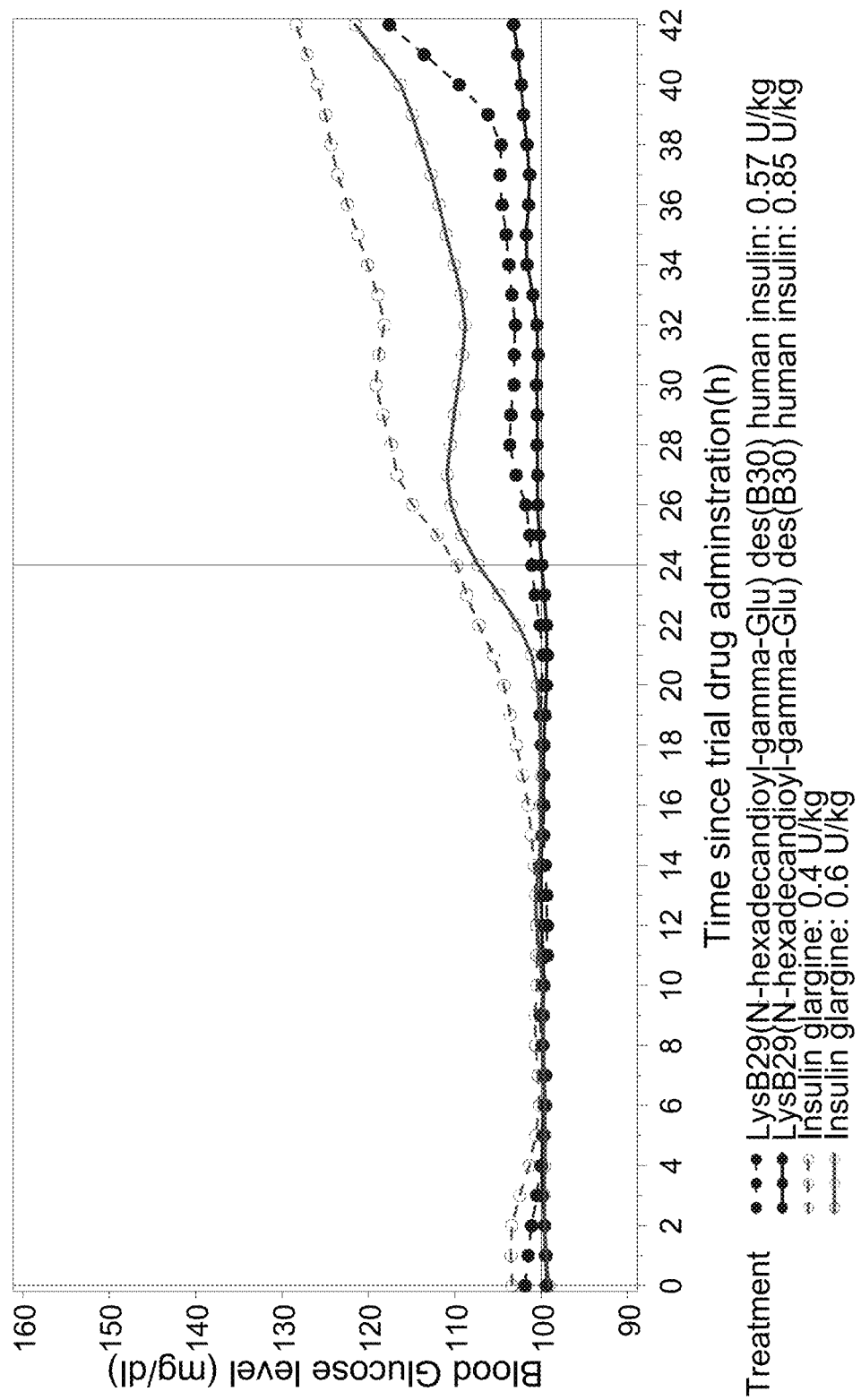
FIG. 2 shows the blood glucose level plotted against the time since the administration of the trial drug.

LysB29(Nε-hexadecandioyl-γ-Glu) des(B30) human insulin appeared to have a flatter and more protracted action profile and a longer duration of action compared with IGlar as evidenced by the GIR profile characteristics shown in FIG. 1. FIG. 1 shows that LysB29(Nε-hexadecandioyl-γ-Glu) des(B30) human insulin has a lower GIRmax at a comparable dose, longer time to GIRmax at both dose levels and less peak to trough range. The duration of action of LysB29(Nε-hexadecandioyl-γ-Glu) des(B30) human insulin under the present circumstances was approximately 40 hours or longer as seen in FIG. 2, which shows that LysB29(Nε-hexadecandioyl-γ-Glu) des(B30) human insulin has the ability to control blood glucose for a longer period. The conclusions based on activity data (pharmacodynamics) are supported by the pharmacokinetic data (longer time to Cmax and longer terminal half-life).

Example 2

Investigating the Clinical Effect of LysB29(Nε-Hexadecandioyl-γ-Glu) Des(B30) Human Insulin Administered Once Daily with Varying Intervals.

Key Methodological Elements and Results

The trial was designed to assess the feasibility, efficacy, safety and tolerability of LysB29(Nε-hexadecandioyl-γ-Glu) des(B30) human insulin (600 nmol/mL) for the treatment of subjects with type 2 diabetes once daily with varying injection intervals (flexible injection). The treatment consisted of administration of insulin with or without metformin and/or sufonylurea and/or pioglitazone, in subjects with type 2 diabetes failing on insulin treatment or oral antidiabetic (OAD) treatment or the combination of insulin and OAD treatment. The feasibility of varying injection intervals (i.e. flexible injection) with LysB29(Nε-hexadecandioyl-γ-Glu) des(B30) human insulin was investigated by having participating subjects inject in the morning (between waking up and breakfast) on Mondays, Wednesdays and Fridays, while injecting in the evening (between evening meal and bedtime) on Tuesdays, Thursdays, Saturdays and Sundays as shown in Table A.

TABLE A

Dosing regime for flexible injection

| | Mondays | Tuesdays | Wednesdays | Thursdays | Fridays | Saturdays | Sundays |
|---|---|---|---|---|---|---|---|
| Time of administration | Morning[1] | Evening[2] | Morning | Evening | Morning | Evening | Evening |

[1]Morning is defined as between waking up and breakfast
[2]Evening is defined as between evening meal and bedtime Primary Objective To assess glucose control with respect to HbA1c after 26 weeks of treatment with LysB29(Nε-hexadecandioyl-γ-Glu) des(B30) human insulin once daily with varying injection intervals (flexible injection), LysB29(Nε-hexadecandioyl-γ-Glu) des(B30) human insulin once daily given with the evening meal or insulin glargine once daily given at the same time each day (according to the approved label), all in combination with metformin and/or sulfonylurea and/or pioglitazone in subjects with type 2 diabetes failing on insulin treatment or oral antidiabetic (OAD) treatment or the combination of insulin and OAD treatment.

Materials and Methods

The trial was performed in subjects with type 2 diabetes, previously treated with one or more of the oral antidiabetic agents: metformin, sulfonylurea, pioglitazone or with any basal insulin treatment or the combination of the OADs specified and any basal insulin treatment. At randomisation, subjects continued their OAD treatment (if any) while adding, starting or switching to basal insulin LysB29(Nε-hexadecandioyl-γ-Glu) des(B30) human insulin once daily with varying injection intervals or LysB29(Nε-hexadecandioyl-γ-Glu) des(B30) human insulin once daily with the evening meal or insulin glargine once daily at the same time each day (according to label).

A total of 687 subjects with type 2 diabetes, age of 56 years, mean duration of diabetes of 10.6 years, mean BMI of 29.6 kg/m$^2$, mean FPG of 8.9 mmol/L, and mean HbA$_{1c}$ of 8.4% were randomised (1:1:1) to receive once-daily LysB29 (Nε-hexadecandioyl-γ-Glu) des(B30) human insulin given with varying injection intervals (229 subjects) or once-daily LysB29(Nε-hexadecandioyl-γ-Glu) des(B30) human insulin given with the evening meal (228 subjects) or once-daily insulin glargine (230 subjects), alone or in combination with metformin and/or SU and/or Pioglitazone, for a treatment period of 26 weeks.

The specific combinations of OAD and insulin treatment prior to randomisation can be seen in Table B. The insulin types used prior to randomisation to the study insulin products are shown in Table C. In table D the OAD(s) used prior to and during the experiment are shown.

TABLE B

Antidiabetic Treatment Regimen at Screening - Full Analysis Set

| | IDeg OD FF | | IDeg OD | | IGlar OD | | Total | |
|---|---|---|---|---|---|---|---|---|
| | N | (%) | N | (%) | N | (%) | N | (%) |
| Number of Subjects | 229 | | 228 | | 230 | | 687 | |
| OAD only | 133 | (58.1) | 131 | (57.5) | 134 | (58.3) | 398 | (57.9) |
| One OAD | 26 | (11.4) | 44 | (19.3) | 33 | (14.3) | 103 | (15.0) |
| Two OADs | 98 | (42.8) | 79 | (34.6) | 89 | (38.7) | 266 | (38.7) |
| Three OADs | 9 | (3.9) | 8 | (3.5) | 11 | (4.8) | 28 | (4.1) |
| Four OADs | | | | | 1 | (0.4) | 1 | (0.1) |
| Basal insulin only | 7 | (3.1) | 8 | (3.5) | 6 | (2.6) | 21 | (3.1) |
| Basal insulin | 7 | (3.1) | 8 | (3.5) | 6 | (2.6) | 21 | (3.1) |
| Basal insulin + at least one OAD | 89 | (38.9) | 88 | (38.6) | 89 | (38.7) | 266 | (38.7) |
| Basal + one OAD | 39 | (17.0) | 31 | (13.6) | 34 | (14.8) | 104 | (15.1) |
| Basal + two OADs | 48 | (21.0) | 55 | (24.1) | 53 | (23.0) | 156 | (22.7) |
| Basal + three OADs | 2 | (0.9) | 2 | (0.9) | 2 | (0.9) | 6 | (0.9) |
| Other | | | 1 | (0.4) | 1 | (0.4) | 2 | (0.3) |
| Premix + one OAD | | | 1 | (0.4) | | | 1 | (0.1) |
| Basal Bolus | | | | | 1 | (0.4) | 1 | (0.1) |

Ideg OD FF - LysB29(Nε-hexadecandioyl-γ-Glu) des(B30) human insulin administered flexibly once daily,
IDeg OD - LysB29(Nε-hexadecandioyl-γ-Glu) des(B30) human insulin administered at the same time once daily,
IGlar OD - Insulin glargine administered at the same time once daily
N: Number of Subjects
%: Proportion of Subjects

TABLE C

Insulin at Screening - Summary - Full Analysis Set

| | IDeg OD FF | | IDeg OD | | IGlar OD | | Total | |
|---|---|---|---|---|---|---|---|---|
| | N | (%) | N | (%) | N | (%) | N | (%) |
| Number of Subjects | 229 | | 228 | | 230 | | 687 | |
| Basal insulin | 96 | (41.9) | 96 | (42.1) | 96 | (41.7) | 288 | (41.9) |
| IDet | 19 | (8.3) | 21 | (9.2) | 21 | (9.1) | 61 | (8.9) |
| IGlar | 43 | (18.8) | 41 | (18.0) | 30 | (13.0) | 114 | (16.6) |
| NPH insulin | 34 | (14.8) | 34 | (14.9) | 45 | (19.6) | 113 | (16.4) |
| Bolus insulin | | | | | 1 | (0.4) | 1 | (0.1) |
| IAsp | | | | | 1 | (0.4) | 1 | (0.1) |
| Premix | | | 1 | (0.4) | | | 1 | (0.1) |

N: Number of Subjects
%: Proportion of Subjects
Subjects can use more than one type of insulin within each group
Insulin NPH: Neutral Protamine Hagedorn

TABLE D

OAD Treatment Type at Baseline and End of Trial

| | IDeg | | | | IGlar | | | |
|---|---|---|---|---|---|---|---|---|
| | Baseline | | End of Trial | | Baseline | | End of Trial | |
| Trial (wk) | N | (%) | N | (%) | N | (%) | N | (%) |
| 3668 (26) FF | | | | | | | | |
| Biguanide | 207 | (90.4) | 206 | (90.0) | 211 | (91.7) | 212 | (92.2) |
| Matformin | 207 | (90.4) | 206 | (90.0) | 211 | (91.7) | 212 | (92.2) |
| DPP-4 inhibitor | | | | | 1 | (0.4) | 1 | (0.4) |
| Sitagliptin | | | | | 1 | (0.4) | 1 | (0.4) |
| Glinide | 10 | (4.4) | 10 | (4.4) | 8 | (3.5) | 7 | (3.0) |
| Repaglinide | 10 | (4.4) | 10 | (4.4) | 8 | (3.5) | 7 | (3.0) |
| Sulphonylurea | 159 | (69.4) | 156 | (68.1) | 157 | (68.3) | 155 | (67.4) |
| Glibenclamide | 55 | (24.0) | 54 | (23.6) | 57 | (24.8) | 55 | (23.9) |
| Gliclazide | 43 | (18.8) | 41 | (17.9) | 39 | (17.0) | 39 | (17.0) |
| Glimepiride | 56 | (24.5) | 56 | (24.5) | 54 | (23.5) | 54 | (23.5) |
| Glipizide | 5 | (2.2) | 5 | (2.2) | 7 | (3.0) | 7 | (3.0) |
| Thiazolidinedione | 13 | (5.7) | 12 | (5.2) | 17 | (7.4) | 16 | (7.0) |
| Pioglitazone | 13 | (5.7) | 12 | (5.2) | 16 | (7.0) | 15 | (6.5) |
| Rosiglitazone | | | | | 1 | (0.4) | 1 | (0.4) |
| 3668 (26) | | | | | | | | |
| Biguanide | 205 | (89.9) | 205 | (89.9) | | | | |
| Metformin | 205 | (89.9) | 205 | (89.9) | | | | |
| Glinide | 14 | (6.1) | 13 | (5.7) | | | | |
| Repaglinide | 14 | (6.1) | 13 | (5.7) | | | | |
| Sulphonylurea | 136 | (59.6) | 136 | (59.6) | | | | |
| Glibenclamide | 51 | (22.4) | 50 | (21.9) | | | | |
| Gliclazide | 37 | (16.2) | 37 | (16.2) | | | | |
| Glimepiride | 44 | (19.3) | 44 | (19.3) | | | | |
| Glipizide | 4 | (1.8) | 4 | (1.8) | | | | |
| Glyburide | | | 1 | (0.4) | | | | |
| Thiazolidinedione | 17 | (7.5) | 17 | (7.5) | | | | |
| Pioglitazone | 17 | (7.5) | 17 | (7.5) | | | | |

Ideg - LysB29(Nε-hexadecandioyl-γ-Glu) des(B30) human insulin
IGlar - insulin glargine,
FF: Fixed injection
End of Trial: a subject's last trial visit excluding the follow-up visit
IGlar (3579, 3672, 3586, 3668) and Sita (3580)
A subject can be on more than one OAD Efficacy Results
HbA$_{1c}$ HbA1c at end of trial and change in HbA1c from baseline to end of trial are given in table 1.

The confidence interval of the treatment contrast when comparing LysB29(Nε-hexadecandioyl-γ-Glu) des(B30) human insulin given with varying injection intervals with the other treatment groups was within the non-inferiority limit 0.4), which is within the non-inferiority limit accepted by the FDA (Guidance for Industry Diabetes Mellitus: Developing Drugs and Therapeutic Biologics for Treatment and Prevention, draft Guidance, U.S. Department of Health and Human Services Food and Drug Administration Center for Drug Evaluation and Research (CDER) February 2008) Thus, the group receiving LysB29(Nε-hexadecandioyl-γ-Glu) des(B30) human insulin given with varying injection intervals was similar to the other two treatment groups with respect to mean changes in $HbA_{1c}$ from baseline to end of treatment (Table 1 and Table 2).

TABLE 1

Mean $HbA_{1c}$ after 26 Weeks of Treatment

| | LysB29(Nε-hexadecandioyl-γ-Glu) des(B30) human insulin Once Daily Flexible Injection[2] | LysB29(Nε-hexadecandioyl-γ-Glu) des(B30) human insulin Once daily with the evening meal | Insulin glargine Once daily Same time each day |
|---|---|---|---|
| $HbA_{1c}$ (%) after 26 weeks of treatment[1] | 7.2 | 7.3 | 7.1 |
| Mean Change from Baseline (% points)[1] | −1.28 | −1.07 | −1.26 |

[1]Arithmetic means.
[2]Flexible injection is as defined in Table A.

TABLE 2

ANOVA[1] of $HbA_{1c}$ after 26 Weeks of Treatment

| | LysB29(Nε-hexadecandioyl-γ-Glu) des(B30) human insulin Once Daily Flexible Injection[2] |
|---|---|
| Treatment Difference vs. Insulin Glargine Once daily Same time each day (HbA1c % points [95% confidence interval]) | 0.04 [−0.12; 0.20] |
| Treatment Difference vs. LysB29(Nε-hexadecandioyl-γ-Glu) des(B30) human insulin Once daily with the evening meal (HbA1c % points [95% confidence interval]) | −0.13 [−0.29; 0.03] |

[1]Results from ANOVA with treatment, anti-diabetic therapy at screening, sex, region, age and baseline HbA1c as explanatory variables.
[2]Flexible injection is as defined in Table A.

Hypoglycaemia

Only six severe hypoglycaemic events were reported during the trial cf. Table 3.

TABLE 3

Overview of Hypoglycaemia

| Hypoglycaemic episodes[1] | LysB29(Nε-hexadecandioyl-γ-Glu) des(B30) human insulin Once Daily Flexible Injection[5] | | | Insulin glargine Once daily Same time each day | | | LysB29(Nε-hexadecandioyl-γ-Glu) des(B30) human insulin Once daily with the evening meal | | |
|---|---|---|---|---|---|---|---|---|---|
| | N[2] | (%)[3] | E[4] | N | (%) | E | N | (%) | E |
| Severe | 1 | (0.4) | 2 | 2 | (0.9) | 2 | 2 | (0.9) | 2 |
| Documented Symptomatic | 149 | (64.8) | 841 | 124 | (54.9) | 770 | 139 | (60.7) | 803 |
| Asymptomatic | 162 | 70.4 | 879 | 159 | (70.4) | 991 | 161 | (70.3) | 892 |
| Probable Symptomatic | 20 | (8.7) | 30 | 15 | (6.6) | 29 | 18 | (7.9) | 32 |
| Relative | 27 | (11.7) | 53 | 24 | (10.6) | 35 | 26 | (11.4) | 78 |
| Unclassifiable | 12 | (5.2) | 15 | 7 | (3.1) | 11 | 7 | (3.1) | 8 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.
[5]Flexible injection is as defined in Table A.

Insulin Dose

TABLE 4

Mean[1] Daily Insulin Dose after 26 Weeks of Treatment

| | LysB29(Nε-hexadecandioyl-γ-Glu) des(B30) human insulin Once daily Flexible injection[2] | LysB29(Nε-hexadecandioyl-γ-Glu) des(B30) human insulin Once daily with the evening meal | Insulin glargine Once daily Same time each day |
|---|---|---|---|
| Daily Dose (U/kg) | 0.55 | 0.52 | 0.52 |

[1]Arithmetic means.
[2]Flexible injection is as defined in Table A.

Conclusions

It was surprisingly found that using LysB29(Nε-hexadecandioyl-γ-Glu) des(B30) human insulin, which has a long duration of action and a peak-less and stable activity profile, subjects with type 2 diabetes were sufficiently regulated with once daily dosing administered with varying injection intervals alone or in combination with OAD treatment.

In subjects with type 2 diabetes failing treatment with OAD and/or insulin 26 weeks treatment with LysB29(Nε-hexadecandioyl-γ-Glu) des(B30) human insulin given flexibly (with varying injection intervals) with or without metformin and/or sulfonylurea and/or pioglitazone, resulted in comparable (non-inferior) glycaemic control and comparable incidence of hypoglycaemic episodes to that observed for LysB29(Nε-hexadecandioyl-γ-Glu) des(B30) human insulin given with the evening meal and to the glycaemic control and the incidence of hypoglycaemic episodes observed for insulin glargine given once daily at the same time each day (according to the approved label).

Example 3

Investigating the Clinical Effect of LysB29(Nε-Hexadecandioyl-γ-Glu) Des(B30) Human Insulin Administered Once Daily with Varying Intervals.

Key Methodological Elements and Results

The trial was designed to assess the feasibility, efficacy, safety and tolerability of LysB29(Nε-hexadecandioyl-γ-Glu) des(B30) human insulin (600 nmol/mL) for the treatment of subjects with type 1 diabetes once daily with varying injection intervals (flexible injection). The treatment consisted of administration of basal insulin (LysB29(Nε-hexadecandioyl-γ-Glu) des(B30) human insulin or insulin glargine) in combination with separate injections of bolus insulin, (AspB28 human insulin). The feasibility of varying injection intervals (i.e. flexible injection) with LysB29(Nε-hexadecandioyl-γ-Glu) des(B30) human insulin was investigated by having participating subjects inject in the morning (between waking up and breakfast) on Mondays, Wednesdays and Fridays, while injecting in the evening (between evening meal and bedtime) on Tuesdays, Thursdays, Saturdays and Sundays as shown in Table B.

combination with AspB28 human insulin in subjects with type 1 diabetes.

Materials and Methods

The trial was performed in subjects with type 1 diabetes, previously treated with insulin for at least 12 months. At randomisation, subjects switched to basal insulin LysB29 (Nε-hexadecandioyl-γ-Glu) des(B30) human insulin once daily with varying injection intervals or LysB29(Nε-hexadecandioyl-γ-Glu) des(B30) human insulin once daily with the evening meal or insulin glargine once daily at the same time each day (according to label) all in combination with AspB28 human insulin.

A total of 490 subjects with type 1 diabetes, age of 56 years, mean duration of diabetes of 10.6 years, mean BMI of 29.6 kg/m$^2$, mean FPG of 8.9 mmol/L, and mean HbA$_{1c}$ of 8.4% were randomised (1:1:1) to receive once-daily LysB29 (Nε-hexadecandioyl-γ-Glu) des(B30) human insulin given with varying injection intervals (164 subjects) or once-daily

TABLE B

Dosing regime for flexible injection

| | Mondays | Tuesdays | Wednesdays | Thursdays | Fridays | Saturdays | Sundays |
|---|---|---|---|---|---|---|---|
| Time of administration | Morning[1] | Evening[2] | Morning | Evening | Morning | Evening | Evening |

[1] Morning is defined as between waking up and breakfast
[2] Evening is defined as between evening meal and bedtime Primary Objective To assess glucose control with respect to HbA1c after 26 weeks of treatment with LysB29(Nε-hexadecandioyl-γ-Glu) des(B30) human insulin once daily with varying injection intervals (flexible injection), LysB29(Nε-hexadecandioyl-γ-Glu) des(B30) human insulin once daily given with the evening meal or insulin glargine once daily given at the same time each day (according to the approved label), all in LysB29(Nε-hexadecandioyl-γ-Glu) des(B30) human insulin given with the evening meal (165 subjects) or once-daily insulin glargine, given according to label, (161 subjects) for a treatment period of 26 weeks.

The specific insulin treatment prior to randomisation can be seen in Table C. The insulin types used prior to randomisation to the study insulin products are shown in Table D.

TABLE C

Anti-diabetic Treatment Regimen at Screening - Full Analysis Set

| | IDeg OD FF | | IDeg OD | | IGlar OD | | Total | |
|---|---|---|---|---|---|---|---|---|
| | N | (%) | N | (%) | N | (%) | N | (%) |
| Number of Subjects | 164 | | 165 | | 164 | | 493 | |
| Basal-Bolus Therapy | 163 | (99.4) | 165 | (100.0) | 164 | (100.0) | 492 | (99.8) |
| Basal TID + Bolus TID or more | 1 | (0.6) | | | | | 1 | (0.2) |
| Basal BID + Bolus TID or more | 50 | (30.5) | 48 | (29.1) | 44 | (26.8) | 142 | (28.8) |
| Basal OD + Bolus TID or more | 112 | (68.3) | 117 | (70.9) | 119 | (72.6) | 348 | (70.6) |
| Basal OD + Premix TID | | | | | 1 | (0.6) | 1 | (0.2) |
| Other | 1 | (0.6) | | | | | 1 | (0.2) |
| Premix BID | 1 | (0.6) | | | | | 1 | (0.2) |

NI: Number of Subjects
%: Proportion of Subjects
OD: Once daily
FF: Flexible injection
IDeg: LysB29(Nε-hexadecandioyl-γ-Glu) des(B30) human insulin
TID: three times a day
BID: two times a day
Premix TID: Any biphasic insulin three times a day
Premix BID:: Any biphasic insulin two times a day

TABLE D

Insulin Type at Screening - Summary - Full Analysis Set

|  | IDeg OD FF | | IDeg OD | | IGlar OD | | Total | |
| --- | --- | --- | --- | --- | --- | --- | --- | --- |
|  | N | (%) | N | (%) | N | (%) | N | (%) |
| Number of Subjects | 164 |  | 165 |  | 164 |  | 493 |  |
| Basal | 163 | (99.4) | 165 | (100.0) | 164 | (100.0) | 492 | (99.8) |
| IGlar | 107 | (65.2) | 107 | (64.8) | 100 | (61.0) | 314 | (63.7) |
| IDet | 44 | (26.8) | 43 | (26.1) | 47 | (28.7) | 134 | (27.2) |
| Insulin NPH | 11 | (6.7) | 14 | (8.5) | 17 | (10.4) | 42 | (8.5) |
| IDet + insulin NPH | 1 | (0.6) |  |  |  |  | 1 | (0.2) |
| HI |  |  | 1 | (0.6) |  |  | 1 | (0.2) |
| Bolus | 163 | (99.4) | 165 | (100.0) | 163 | (99.4) | 491 | (99.6) |
| IAsp | 77 | (47.0) | 86 | (52.1) | 88 | (53.7) | 251 | (50.9) |
| ILis | 61 | (37.2) | 68 | (41.2) | 61 | (37.2) | 190 | (38.5) |
| HI | 14 | (8.5) | 6 | (3.6) | 7 | (4.3) | 27 | (5.5) |
| IGlu | 11 | (6.7) | 5 | (3.0) | 7 | (4.3) | 23 | (4.7) |
| Premix | 1 | (0.6) |  |  | 1 | (0.6) | 2 | (0.4) |
| BIAsp | 1 | (0.6) |  |  | 1 | (0.6) | 2 | (0.4) |

N: Number of Subjects
%: Proportion of Subjects
Subjects can use more than one type of insulin within each group
BIAsp: Biphasic Insulin Aspart,
HI: Human Insulin
IAsp: Insulin Aspart,
IDet: Insulin Detemir,
IGlar: Insulin Glargine
IGlu: Insulin Glulisine,
ILis: Insulin Lispro
Insulin NPH: Neutral Protamine Hagedorn
Premix: Any biphasic insulin Efficacy Results $HbA_{1c}$ $HbA1c$ at end of trial and change in HbA1c from baseline to end of trial are given in table 3. The confidence interval of the treatment contrast when comparing LysB29(Nε-hexadecandioyl-γ-Glu) des(B30) human insulin given with varying injection intervals with the other treatment groups was within the non-inferiority limit of 0.4 (Table 4).

TABLE 3

Mean $HbA_{1c}$ after 26 Weeks of Treatment

|  | LysB29(Nε-hexadecandioyl-γ-Glu) des(B30) human insulin Once Daily Flexible Injection[2] | LysB29(Nε-hexadecandioyl-γ-Glu) des(B30) human insulin Once daily with the evening meal | Insulin glargine Once daily Same time each day |
| --- | --- | --- | --- |
| $HbA_{1c}$ (%) after 26 weeks of treatment[1] | 7.31 | 7.30 | 7.14 |
| Mean Change from Baseline (% points)[1] | −0.40 | −0.41 | −0.57 |

[1]Arithmetic means.
[2]Flexible injection is as defined in Table A.

TABLE 4

ANOVA[1] of $HbA_{1c}$ after 26 Weeks of Treatment

|  | LysB29(Nε-hexadecandioyl-γ-Glu) des(B30) human insulin Once Daily Flexible Injection[2] |
| --- | --- |
| Treatment Difference vs. Insulin Glargine Once daily Same time each day (HbA1c % points [95% confidence interval]) | 0.17 [0.04; 0.30] |
| Treatment Difference vs. LysB29(Nε-hexadecandioyl-γ-Glu) des(B30) human insulin Once daily with the evening meal (HbA1c % points [95% confidence interval]) | 0.01 [−0.13; 0.14] |

[1]Results from ANOVA with treatment, anti-diabetic therapy at screening, sex, region, age and baseline HbA1c as explanatory variables.
[2]Flexible injection is as defined in Table A.

Hypoglycaemia

Table 5 shows the hypoglycaemic events that were reported during the trial.

TABLE 5

Overview of Hypoglycaemia

| Hypoglycaemic episodes[1] | LysB29(Nε-hexadecandioyl-γ-Glu) des(B30) human insulin Once Daily Flexible Injection[5] | | | Insulin glargine Once daily Same time each day | | | LysB29(Nε-hexadecandioyl-γ-Glu) des(B30) human insulin Once daily with the evening meal | | |
|---|---|---|---|---|---|---|---|---|---|
| | N[2] | (%)[3] | E[4] | N | (%) | E | N | (%) | E |
| Severe | 17 | (10.4) | 25 | 16 | (9.9) | 37 | 21 | (12.7) | 28 |
| Documented Symptomatic | 154 | (93.9) | 7471 | 153 | (95.0) | 7964 | 161 | (97.6) | 9467 |
| Asymptomatic | 134 | (81.7) | 3982 | 131 | (81.4) | 3978 | 139 | (84.2) | 3763 |
| Probable Symptomatic | 26 | (15.9) | 64 | 24 | (14.9) | 124 | 28 | (17.0) | 171 |
| Relative | 9 | (5.5) | 36 | 7 | (4.3) | 11 | 10 | (6.1) | 20 |
| Unclassifiable | 90 | (54.9) | 682 | 87 | (54.0) | 805 | 94 | (57.0) | 871 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.
[5]Flexible injection is as defined in Table A.

Insulin Dose

TABLE 6

Mean[1] Daily Insulin Dose after 26 Weeks of Treatment

| | LysB29(Nε-hexadecandioyl-γ-Glu) des(B30) human insulin Once daily Flexible injection[2] | Insulin glargine Once daily Same time each day | LysB29(Nε-hexadecandioyl-γ-Glu) des(B30) human insulin Once daily with the evening meal |
|---|---|---|---|
| Daily Basal Insulin Dose (U/kg) | 0.42 | 0.42 | 0.38 |
| Daily Prandial Insulin Dose (U/kg) | 0.35 | 0.42 | 0.33 |

[1]Arithmetic mean.
[2]Flexible injection is as defined in Table A.

Conclusions

It was surprisingly found that using LysB29(Nε-hexadecandioyl-γ-Glu) des(B30) human insulin, which has a long duration of action and a peak-less and stable activity profile, subjects with type 1 diabetes were sufficiently regulated with once daily dosing administered with varying injection intervals in combination with bolus insulin.

In subjects with type 1 diabetes 26 weeks treatment with LysB29(Nε-hexadecandioyl-γ-Glu) des(B30) human insulin given flexibly (with varying injection intervals) in combination with AspB28 human insulin, resulted in non-inferior glycaemic control and comparable incidence of hypoglycaemic episodes to that observed for LysB29(Nε-hexadecandioyl-γ-Glu) des(B30) human insulin given with the evening meal and to the glycaemic control and the incidence of hypoglycaemic episodes observed for insulin glargine given once daily at the same time each day (according to the approved label).

Example 4

Investigating the Clinical Effect of the Co-Formulated Combination Product of LysB29(Nε-Hexadecandioyl-γ-Glu) Des(B30) Human Insulin and AspB28 Human Insulin Administered in Relation to Meals with the Option to Change Between Meals from Day to Day During the Treatment Period.

Key Methodological Elements and Results

The trial was designed to assess the feasibility, efficacy, safety and tolerability of combination product of LysB29 (Nε-hexadecandioyl-γ-Glu) des(B30) human insulin and AspB28 human insulin (600 nmol/mL) for the treatment of subjects with type 1 diabetes once daily given in relation to a meal with the option to change from day to day the injection time for the combination product of LysB29(Nε-hexadecandioyl-γ-Glu) des(B30) human insulin and AspB28 human insulin to a different meal. The treatment consisted of the administration of the combination product of LysB29 (Nε-hexadecandioyl-γ-Glu) des(B30) human insulin and AspB28 human insulin at one meal and Asp28 human insulin given in relation to remaining insulin-requiring meals in subjects with type 1 diabetes.

Primary Objective

To assess glucose control with respect to HbA1c after 26 weeks of treatment with combination product of LysB29 (Nε-hexadecandioyl-γ-Glu) des(B30) human insulin and AspB28 human insulin in relation to a selected meal (with the option of varying the meal from day to day) or insulin detemir once daily (with the option to optimise to twice daily in not optimally controlled), both treatment arms in combination with Asp28 human insulin with remaining insulin-requiring meals in subjects with type 1 diabetes.

Materials and Methods

The trial was performed in subjects with type 1 diabetes having been diagnosed at least one year prior to entering the trial with an $HbA_{1c}$ between 7 and 10%. At randomisation, subjects were allocated to either of two basal insulin products:

1. the combination of LysB29(Nε-hexadecandioyl-γ-Glu) des(B30) human insulin and AspB28 human insulin once daily with any meal (varying injection time from day to day) or 2. insulin detemir once daily (or twice daily) at the same time each day (according to label). Both treatment arms received AspB28 human insulin as meal time insulin at remaining meals.

A total of 548 subjects with type 1 diabetes, age of 41 years, mean duration of diabetes of 17 years, mean BMI of 26.4 kg/m², mean FPG of 10.5 mmol/L, and mean HbA$_{1c}$ of 8.3% were randomised (2:1 in favour of the combination of LysB29(Nε-hexadecandioyl-γ-Glu) des(B30) human insulin and AspB28 human insulin for a treatment period of 26 weeks.

Efficacy Results

HbA$_{1c}$

The confidence interval of the treatment contrast when comparing LysB29(Nε-hexadecandioyl-γ-Glu) des(B30) human insulin and AspB28 human insulin with the other treatment group was within the non-inferiority limit of 0.4. The two groups were therefore similar with respect to mean changes in HbA$_{1c}$ from baseline to end of treatment (statistical analysis Table 5).

TABLE 5

Treatment difference between treatment groups in HbA1c (%) at end of trial

| | LysB29(Nε-hexadecandioyl-γ-Glu) des(B30) human insulin and AspB28 human insulin |
|---|---|
| Treatment Difference vs. insulin detemir[1] (HbA1c % points [95% confidence intervals]) | −0.05 [−0.18; 0.08] |

[1]Results from ANOVA with treatment, anti-diabetic therapy at screening, sex, region, age and baseline HbA1c as explanatory variables Hypoglycaemia Hypoglycaemic episodes were registered during the trial according to the definitions of American Diabetes Association, cf. Table 6.

TABLE 6

Overview of Hypoglycaemia. Randomisation was 2:1 (LysB29(Nε-hexadecandioyl-γ-Glu) des(B30) human insulin and AspB28 human insulin:insulin detemir)

| Hypoglycaemic episodes[1] | LysB29(Nε-hexadecandioyl-γ-Glu) des(B30) human insulin and AspB28 human insulin | | | Insulin Detemir | | |
|---|---|---|---|---|---|---|
| | N[2] | (%)[3] | E[4] | N | (%) | E |
| Severe | 35 | 9.7 | 56 | 22 | 12.2 | 35 |
| Documented Symptomatic | 319 | 88.1 | 9670 | 156 | 86.7 | 5126 |
| Asymptomatic | 270 | 74.6 | 4032 | 137 | 76.1 | 1804 |
| Probable Symptomatic | 71 | 19.6 | 234 | 40 | 22.2 | 149 |
| Relative | 42 | 11.6 | 108 | 17 | 9.4 | 33 |
| Unclassifiable | 105 | 29.0 | 395 | 50 | 27.8 | 241 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.

Insulin Dose

TABLE 7

Mean[1] Total Daily Insulin Dose after 26 Weeks of Treatment

| | LysB29(Nε-hexadecandioyl-γ-Glu) des(B30) human insulin and AspB28 human insulin + AspB28 human insulin | Insulin Detemir + AspB28 human insulin |
|---|---|---|
| Daily Dose (U/kg) | 0.86 | 1.00 |

[1]Arithmetic mean.

Conclusion

It was surprisingly found that the basal component of the combination product, LysB29(Nε-hexadecandioyl-γ-Glu) des(B30) human insulin, which has a long duration of action and a peak-less and stable activity profile, enabled subjects to be sufficiently regulated with once daily dosing even when varying the injection intervals as a result of changing the meal at which injection of the combination product was administered.

In subjects with type 1 diabetes insulin 26 weeks treatment with LysB29(Nε-hexadecandioyl-γ-Glu) des(B30) human insulin combined with AspB28 human insulin given once daily in relation to a selected meal (with the option of varying the injection time to a different meal from day to day) resulted in comparable (non-inferior) glycaemic control to that of insulin detemir given twice daily according to label, both treatment were combined with AspB28 human insulin for the remaining meals. The combination of LysB29 (Nε-hexadecandioyl-γ-Glu) des(B30) human insulin resulted in lower insulin use and a lower incidence of hypoglycaemic episodes compared to that observed for insulin detemir.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A method of treating type 1 or type 2 diabetes comprising:
   administering to a patient in need thereof a pharmaceutically effective dosage of a derivative of a naturally occurring insulin or of an insulin analogue, wherein said insulin derivative exhibits a prolonged profile of action and wherein said dosages are administered at intervals, wherein at least one of said intervals has a length of
 i. at least 1.3 times the mean of said intervals, or
 ii. no more than 0.85 times the mean of said intervals,
wherein the mean of said intervals is at least 12 hours, and less than 36 hours,
wherein said dosage is not adjusted between administrations, and
wherein said derivative of said naturally occurring insulin or said insulin analogue is LysB29(Nεhexadecandioyl-γ-Glu) des(B30) human insulin.

2. A method of treating type 1 or type 2 diabetes according to claim 1, wherein at least one of said intervals has a length of at least 1.35 times the mean of said intervals, at least 1.4 times the mean of said intervals, or at least 1.45 times the mean of said intervals.

3. A method of treating type 1 or type 2 diabetes according to claim 1, wherein at least one of said intervals is no more than 0.80 times the mean of said intervals, no more than 0.75 times the mean of said intervals, or no more than 0.70 times the mean of said intervals.

4. A method of treating type 1 or type 2 diabetes according to claim 1, wherein administration of the insulin derivative exhibiting a prolonged profile of action is supplemented with more frequent administrations of a fast-acting naturally occurring insulin, insulin analogue or derivative, and/or administration of a non-insulin anti-diabetic drug.

5. A method of treating type 1 or type 2 diabetes according to claim 4, wherein said fast acting naturally occurring insulin, insulin analogue or derivative and/or administration of a non-insulin antidiabetic drug is insulin aspart (AspB28 human insulin).

6. A method of treating type 1 or type 2 diabetes according to claim 5, wherein the LysB29(Nε-hexadecandioyl-γ-Glu) des(B30) human insulin and the insulin aspart (AspB28 human insulin) is mixed in a ratio of 70/30%.

7. A method of treating type 1 or type 2 diabetes according to claim 6, wherein the LysB29(Nε-hexadecandioyl-γ-Glu) des(B30) human insulin and the insulin aspart (AspB28 human insulin) mixture is formulated together with a pharmaceutically acceptable carrier and/or vehicle and/or diluent and/or excipient.

8. A method of treating type 1 or type 2 diabetes according to claim 1, wherein the insulin derivative is formulated together with a pharmaceutically acceptable carrier, and/or vehicle, and/or diluent, and/or excipient.

9. A method of treating type 1 or type 2 diabetes according to claim 1, wherein substantially no other naturally occurring insulin, insulin analogue or derivative of naturally occurring insulin or insulin analogue exhibiting a prolonged profile of action is administered to said patient.

* * * * *